United States Patent [19]

Ashmore

[11] Patent Number: 4,781,750

[45] Date of Patent: Nov. 1, 1988

[54] HERBICIDALLY ACTIVE ENOLS

[75] Inventor: John W. Ashmore, Souderton, Pa.

[73] Assignee: Rohm and Haas Company, Philadelphia, Pa.

[21] Appl. No.: 770,033

[22] Filed: Aug. 27, 1985

[51] Int. Cl.$^4$ ............... A01N 33/12; A01N 37/43
[52] U.S. Cl. .................................. 71/85; 71/88; 71/90; 71/92; 71/95; 71/97; 71/103; 71/105; 71/106; 71/118; 544/176; 544/386; 548/530; 549/78; 549/505; 558/401; 556/117; 525/295
[58] Field of Search ............ 558/401; 556/117; 525/295; 544/176, 386; 548/530; 71/97, 105, 103, 85, 90, 88, 92, 95, 106, 118

[56] References Cited

U.S. PATENT DOCUMENTS

| | | | |
|---|---|---|---|
| 3,723,498 | 3/1973 | Joos | 556/117 |
| 4,447,450 | 5/1984 | Ho | 260/465.4 |
| 4,508,659 | 4/1985 | Rowson et al. | 260/465 D |

FOREIGN PATENT DOCUMENTS

| | | |
|---|---|---|
| 0104432 | 4/1984 | European Pat. Off. |
| 184480 | 4/1985 | Japan |

OTHER PUBLICATIONS

Chemical Abstracts, 88:37534v (1978).
Chemical Abstracts, 78:135600b (1973).
Chemical Abstracts, 75:140805q (1971).
Chemical Abstracts, 72:31389z (1970).
Chemical Abstracts, 75:19862c (1971).
Chemical Abstracts, 75:48060v (1971).
Chemical Abstracts, 76:13382v (1972).
Chemical Abstracts, 85:21548e (1976).
Chemical Abstracts, 96:141933a (1982).
Chemical Abstracts, 97:6255m (1982).

Primary Examiner—Anton H. Sutto
Attorney, Agent, or Firm—Barbara V. Maurer

[57] ABSTRACT

Enols, their geometric isomers, tautomers and halogen addition products having the formula

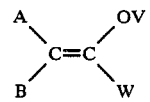

as defined herein and compositions containing these compounds exhibit herbicidal activity.

26 Claims, No Drawings

HERBICIDALLY ACTIVE ENOLS

BACKGROUND OF THE INVENTION

The present invention relates to novel enols, their geometric isomers, tautomers and halogen addition products which have herbicidal activity, compositions which contain these compounds as active ingredients and to a method of selectively controlling weeds which comprises the use of the novel compounds or of compositions containing those compounds.

From European Patent application No. 83108306.8, Publication No. 0 104 432, certain styrene derivatives are disclosed as plant growth regulators and herbicides.

The herbicidal effectiveness of a given styrene derivative, however, cannot be predicted from an examination of the substituent groups attached. Frequently, closely related compounds will demonstrate quite different weed control capabilities. Various compounds may overlap or have complimentary areas of activity or selectivity, and therefore, be useful in combination to control a variety of weeds upon application of a single composition.

Furthermore, previously known sytrene derivatives are not completely effective. An ideal herbicide should provide selective weed control over its full growing season with a single administration at low dosages of application. It should be able to control all common weeds by killing them as the seed, the germinating seed, the seedling, and the growing plant. At the same time, the herbicide should not be phytotoxic to the crops to which it is applied and should decompose or otherwise dissipate so as not to poison the soil permanently. The known styrene derivative herbicides fall short of these ideals. It would be desirable to have new herbicides which show even more selective control of undesirable plants among desirable crop plants or which complement the known styrene derivatives in activity.

The compounds of this invention are capable of controlling plants which were not or are not satisfactorily controlled with known compounds. Previously known styrene derivatives are either too aggressive toward sensitive cultivated plants, or, if they are well tolerated are insufficiently active against the weeds to be controlled.

Surprisingly, the active substances according to the present invention are distinguished from the known styrene derivatives by distinctly better tolerance by cultivated plants, (that is to say better selectivity) and by being more active against weeds, particularly pre-emergence.

Accordingly, one object of the present invention is to provide novel enols which are superior to known compounds of similar structure in respect of their herbicidal action and are better tolerated by important cultivated plants.

SUMMARY OF THE INVENTION

In accordance with the present invention, there is provided novel enols, their geometric isomers, tautomers and halogen addition products having the formula:

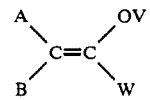

wherein:

A is $COR^1$; $CO_2R^1$; or $CONR^4R^5$;

B is cyano; COR; $CO_2R$; or $S(O)_nR^2$;

V is hydrogen; $(C_1-C_6)$alkyl; alkylcarbonylalkyl having independently, one to four carbon atoms in each alkyl group; alkoxycarbonylalkyl having, independently, one to four carbon atoms in each alkyl group; $COR^3$; or phenalkyl having one to four carbon atoms in the alkyl group;

W is unsubstituted or unsubstituted five to six membered heterocycle comprising three to five nuclear carbon atoms and from one to three of the same or different hetero atoms selected from nitrogen, oxygen or sulfur having one to three of the same or different halo, nitro or $(C_1-C_4)$alkyl; or a substituted phenyl having the formula

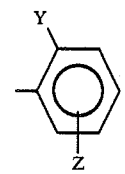

where

Y is halo, nitro, $(C_1-C_4)$haloalkyl, $(C_1-C_4)$alkoxy, $(C_1-C_4)$haloalkoxy or $(C_1-C_4)$alkylcarbonyl; and Z is one to four of the same or different hydrogen, halo, nitro, cyano, $S(O)_nR^2$, $OS(O)_nR^2$, $(C_1-C_6)$alkyl, $(C_1-C_6)$alkoxy, $(C_1-C_6)$haloalkyl, $(C_1-C_6)$haloalkoxy, carboxy, $(C_1-C_6)$alkylcarbonyloxy, $(C_1-C_6)$alkoxycarbonyl, $(C_1-C_6)$alkylcarbonyl, amino, $(C_1-C_6)$alkylamino, $(C_1-C_6)$dialkylamino having independently the stated number of carbon atoms in each alkyl group, $(C_1-C_6)$alkylcarbonylamino, $(C_1-C_6)$alkoxycarbonylamino, $(C_1-C_6)$alkylaminocarbonylamino, $(C_1-C_6)$dialkylaminocarbonylamino having independently the stated number of carbon atoms in each alkyl group, $(C_1-C_6)$alkoxycarbonyloxy, $(C_1-C_6)$alkylaminocarbonyloxy, $(C_1-C_6)$dialkylaminocarbonyloxy, unsubstituted or substituted arylcarbonyl having one to five of the same or different halo, nitro, cyano, $S(O)_nR^2$, $(C_1-C_6)$alkyl, $(C_1-C_6)$alkoxy, $(C_1-C_6)$haloalkyl, $(C_1-C_6)$haloalkoxy, carboxy, $(C_1-C_6)$alkylcarbonyloxy, $(C_1-C_6)$alkylcarbonyl, $(C_1-C_6)$alkoxycarbonyl, $(C_1-C_6)$alkylcarbonylamino, amino, $(C_1-C_6)$alkylamino or $(C_1-C_6)$dialkylamino having independently the stated number of carbon atoms in each alkyl group, unsubstituted or substituted arylcarbonyloxy having one to five of the same or different halo, nitro, cyano, $S(O)_nR^2$, $(C_1-C_6)$alkyl, $(C_1-C_6)$alkoxy, $(C_1-C_6)$haloalkyl, $(C_1-C_6)$haloalkoxy, carboxy, $(C_1-C_6)$alkylcarbonyloxy, $(C_1-C_6)$alkylcarbonyl, $(C_1-C_6)$alkoxycarbonyl, $(C_1-C_6)$alkylcarbonylamino, amino, $(C_1-C_6)$alkylamino or $(C_1-C_6)$dialkylamino having independently the stated number of carbon atoms in each alkyl group; unsubstituted or substituted arylcarbonylamino having one to five of the same or different halo, nitro, cyano, $S(O)_nR^2$, $(C_1-C_6)$alkyl, $(C_1-C_6)$alkoxy, $(C_1-C_6)$haloalkyl, $(C_1-C_6)$haloalkoxy, carboxy, $(C_1-C_6)$alkylcarbonyloxy, $(C_1-C_6)$alkylcarbonyl, $(C_1-C_6)$alkoxycarbonyl, $(C_1-C_6)$alkylcarbonylamino, amino, $(C_1-C_6)$alkylamino or $(C_1-C_6)$dialkylamino having independently the stated number of carbon atoms in each alkyl group; unsubstituted or substituted phenoxy having one to five of the same or different halo, nitro, cyano, $S(O)_nR^2$, $(C_1-C_6)$alkyl, $(C_1-C_6)$alkoxy, $(C_1-C_6)$haloalkyl, $(C_1-C_6)$haloalkoxy, carboxy, $(C_1-C_6)$alkylcarbonyloxy, $(C_1-C_6)$alkylcarbonyl, $(C_1-C_6)$alkoxycarbonyl, $(C_1-C_6)$alkylcarbonylamino, amino, $(C_1-C_6)$alkylamino or $(C_1-C_6)$dialkylamino having independently the stated number of carbon atoms in each group;

R is hydrogen or $(C_1-C_4)$alkyl;

$R^1$ is $(C_1-C_4)$alkyl or unsubstituted or substituted $(C_3-C_4)$cycloalkyl where the substituent is halo, cyano or $(C_1-C_2)$alkyl;

$R^2$ is independently $(C_1-C_4)$alkyl; $(C_1-C_4)$haloalkyl; $(C_1-C_4)$cyanoalkyl; unsubstituted or substituted $(C_3-C_8)$cycloalkyl where the substituent is halo, cyano or $(C_1-C_4)$alkyl; or unsubstituted or substituted phenyl having one to three of the same or different halo, nitro, cyano, trifluoromethyl; $(C_1-C_4)$alkyl, $(C_1-C_4)$alkoxy or $S(O)_nR^2$;

$R^3$ is $(C_1-C_6)$alkyl; $(C_1-C_6)$haloalkyl; $(C_1-C_6)$alkoxy; amino; $(C_1-C_6)$alkylamino; dialkylamino having, independently, up to six carbon atoms in each alkyl moiety; or unsubstituted or substituted aryl having one to five of the same or different halo, nitro, cyano, $S(O)_nR^2$, $(C_1-C_6)$alkyl, $(C_1-C_6)$alkoxy, $(C_1-C_6)$haloalkyl, carboxy, $(C_1-C_6)$alkanoyloxy or $(C_1-C_6)$alkoxycarbonyl;

$R^4$ and $R^5$ are independently $(C_1-C_3)$alkyl or $R^4$ and $R^5$ can be joined together with the nitrogen to which they are attached to form a heterocycle containing from 3 to 6 nuclear carbon atoms and from 0 to 2 additional hetero atoms selected form nitrogen, oxygen or sulfur;

n is from 0 to 2; and agronomically acceptable salts thereof.

DETAILED DESCRIPTION OF THE PREFERRED EMBODIMENTS

The novel compounds of the present invention have been found to show unexpected activity as weed control agents. By geometric isomers and tautomers is meant compounds of Formula I that may give rise to geometric isomers around the enolic double bond or can exist in more than one tautomer. For example:

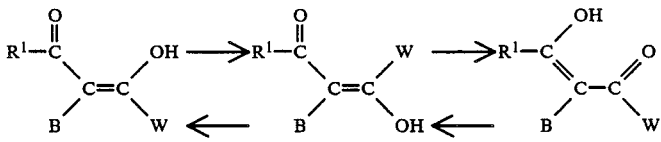

By halogen addition products is meant the compound obtained when halogen ($X_2$ is chlorine, fluorine, bromine or iodine) is added across the enolic double bond. For example:

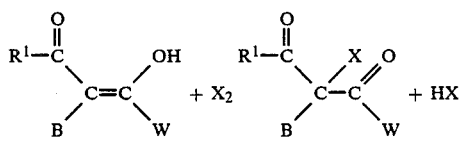

As used herein, a substituent including an alkyl moiety should be understood as including straight or branched chain alkyl groups such as methyl, ethyl, n-propyl, isopropyl, n-butyl, sec-butyl, isobutyl, tert-butyl, neopentyl and the like. The term "halo" includes chloro, fluoro, bromo and iodo. The term "haloalkyl" should be understood as including an alkyl group having one or more halo atoms bonded thereto up to and including perhaloalkyl. Similary, "haloalkoxy" includes an alkoxy group having one or more halo atoms bonded to the alkyl moiety up to and including perhaloalkoxy.

The term "aryl" should be understood as including phenyl, naphthyl and five to six membered heterocycles containing three to five nuclear carbon atoms and from one to three hetero atoms selected from nitrogen, oxygen or sulfur. Representative examples of 5 and 6 membered heterocycles include pyrrolyl, furanyl, thiophenyl, imidazolyl, oxazolyl, thiazolyl, piperazolyl, pyridyl, pyrimidyl and the like. As stated above, an aryl group may be substituted with one or more substituents listed, examples of which include: 2,4-dichlorophenyl, 2-nitrophenyl, 2-trifluoromethylphenyl, 2-nitro-4-chlorophenyl, 2-nitro-4-trifluoromethylphenyl, 2-nitro-4-difluoromethoxyphenyl, 2-nitro-4-trifluoromethoxyphenyl, 2-nitro-4-cyanophenyl, 2-nitro-4-acetoxyphenyl, 2-nitro-4-bromodifluoromethoxyphenyl, 2-trifluoromethyl-4-chlorophenyl, 2-acetyl-4-chlorophenyl, 2-nitro-3-methyl-4-chlorophenyl, 2-nitro-4-chloro-5-methylphenyl, 2-nitro-4-chloro-5-methoxyphenyl, 2-nitro-4-chloro-5-methoxycarbonylphenyl, 2-nitro-4-chloro-5-methylsulfonylphenyl, 2-(3-chloronaphthalene), 2-(3-nitronaphthalene), 2-nitro-3,5-dimethyl-4-chlorophenyl, 2-nitro-4-pentafluoroethylphenyl, 2-nitro-4-n-propylphenyl, 2-nitro-4-n-butoxyphenyl, 2,4-ditrifluoromethylphenyl, and the like.

Representative examples of substituted heteroaromatics include: 2-(4-chloropyridyl), 2-(4-trifluoromethylpyridyl), 2-(4-difluoromethoxypyridyl), 4-(3-nitropyridyl), 4-(3-trifluoromethyl)pyridyl, 2-(5-chloropyrimidyl), 5-(2-chloropyrimidyl), 5-(2-chloro-4-nitropyridyl), 3-(6-chloropyridazinyl), 3-(4-nitro-6-chloropyridazinyl), 2-(5-chloropyrazinyl), 2-(3-nitro-5-chloropyrazinyl), 3-(6-chloro-1,2,4-triazinyl), 3-(6-chloro-1,2,4,5-tetrazinyl), 3-(2-nitro-5-chloro-thiophenyl), 3-(2-nitro-5-chlorofuryl), 3-(2-nitro-5-chloropyrrolyl), 4-(2-chloro-5-nitrothiazolyl), 5-(2-chloro-4-nitrothiazolyl), 4-(5-nitrooxazolyl), 5-(4-nitrooxazolyl), 3-(5-chloro-1,2,4-triazolyl), 2-(4-chloroimidazolyl), and the like.

Since the enols of Formula I may possess acidic or basic functional groups, they can form novel acid salts with appropriate bases or acids which also exhibit herbicidal activity. Typical salts are the agronomically acceptable metal salts, ammonium salts, sulfonium salts, sulfoxonium salts and phosphonium salts. Among the metal salts are those in which the metal cation is an alkali metal cation such as sodium, potassium, lithium or the like, an alkaline earth metal cation such as calcium, magnesium, barium, strontium, or the like, or a heavy metal cation such as zinc, manganese, cupric, cuprous, ferric, ferrous, titanium, aluminum or the like. Among the sulfonium and sulfoxonium salts are those in which the sulfonium or sulfoxonium cation has the formula $S(O)_j(R^{10})_3$ where j is 0 or 1 and each $R^{10}$ independently is a (C$_1$-C$_6$)alkyl group, a phenyl group. Among the phosphonium salts are those in which the phosphonium cation has the formula (R$^{12}$)$_4$P(O)$_j$ where j is 0 or 1 and each R$^{12}$ is independently a (C$_1$-C$_6$)alkyl group, (C$_1$-C$_4$)alkoxy group or a phenyl group. Particularly preferred salts include lithium, magnesium, copper and ammonium. Among the ammonium salts are those in which the ammonium cation has the formula NR$^{13}$R$^{14}$R$^{15}$R$^{16}$ wherein each of R$^{13}$, R$^{14}$, R$^{15}$ and R$^{16}$ are independently a hydrogen atom, a (C$_1$-C$_{20}$)alkyl group, a (C$_3$-C$_8$)alkenyl group, a (C$_3$-C$_8$)alkynyl group, a (C$_2$-C$_8$)hydroxyalkyl group, a (C$_2$-C$_8$)alkoxyalkyl group, a (C$_2$-C$_6$)aminoalkyl group, a (C$_2$-C$_6$)haloalkyl group, an amino group, a (C$_1$-C$_4$)alkyl or di(C$_1$-C$_4$)alkylamino group, a substituted or unsubstituted phenyl group, a substituted or unsubstituted phenylalkyl group, having up to four carbon atoms in the alkyl moiety, or any two of R$^{13}$, R$^{14}$, R$^{15}$ or R$^{16}$ can be taken together to form with the nitrogen atom a 5- or 6-member heterocyclic ring, optionally having up to one additional hetero oxygen, nitrogen, or sulfur atom in the ring, and preferably saturated, such as piperidino, morpholino, pyrrolidino, or piperazino ring or the like, or any three of R$^{13}$, R$^{14}$, R$^{15}$ or R$^{16}$ can be taken together to form with the nitrogen atom a 5- or 6-member aromatic heterocyclic ring, such as a pyrrazole or pyridine ring. When the ammonium group contains a substituted phenyl or substituted phenylalkyl group, the substituents will generally be selected from halogen atoms, (C$_1$-C$_8$)alkyl groups, (C$_1$-C$_4$)alkoxy groups, hydroxy groups, nitro groups, trifluoromethyl groups, cyano groups, amino groups, (C$_1$-C$_4$)alkylthio groups, and the like. Such substituted phenyl groups preferably have up to two such substituents. Representative ammonium cations include ammonium, dimethylammonium, 2-ethylhexylammonium, bis(2-hydroxyethyl)ammonium, tris(2-hydroxyethyl)ammonium, dicyclohexylammonium, t-octylammonium, 2-hydroxyethylammonium, morpholinium, piperidinium, 2-phenethylammonium, 2-methylbenzylammonium, n-hexylammonium, triethylammonium, trimethylammonium, tri(n-butyl)ammonium, methoxyethylammonium, diisopropylammonium, pyridinium, dialkylammonium, pyrazolium, propargylammonium, dimethylhydrazinium, octadecylammonium, 4-dichlorophenylammonium, 4-nitrobenzylammonium, benzyltrimethylammonium, 2-hydroxyethyldimethyloctadecylammonium, 2-hydroxyethyldiethyloctylammonium, decyltrimethylammonium, hexyltriethylammonium, 4-methylbenzyltrimethylammonium, and the like. Among the acid addition salts are those in which the anion is an agronomically acceptable anion such as chloride, bromide, sulfate, nitrate, perchlorate, acetate, oxalate and the like.

Examples of the compounds of the present invention embraced by Formula I include:
N,N-dimethyl-alpha-methylcarbonyl-beta-hydroxy-2-nitro-4-chlorocinnamamide;
Azetidino-alpha-cyano-beta-oxido-2-nitro-4-trifluoromethylcinnamamide lithium salt;
N,N-dimethyl-alpha-ethoxycarbonyl-beta-(2-propynyloxy)-2-trifluoromethyl-4-chlorocinnamamide;
Methyl-alpha-cyano-beta-(2-methylbenzoyloxy)-2-nitro-4-chlorodifluoromethoxycinnamate;
1-[4-(3-nitro)pyridyl]-1-acetoxy-2-cyano-4-methyl-1-penten-3-one;
1-(2,4-dichlorophenyl)-1-methoxy-2-cyano-4,4-dimethyl-1-penten-3-one;
1-[6-(7-nitro)quinolinyl]-1-benzoyloxy-2-methylcarbonyl-4,4-dimethyl-1-penten-3-one;
1-[7-(4-chloro-1-hydroxy)benztriazolyl]-1-benzyloxy-2-methoxycarbonyl-4,4-dimethyl-1-penten-3-one;
bis 1-[3-(2-nitro-5-chloro)thiophenyl]-1-oxido-2-methylthio-4,4-dimethyl-1-penten-3-one zinc (II) salt;
1-(2-nitro-4-chloro-5-methoxycarbonylphenyl-1-methoxycarbonyloxy-2-fluoro-4,4-dimethyl-1-penten-3-one;
2-cyclopropylcarbonyl-3-methoxymethoxy-3-[5-(4-trifluoromethyl)-isothiazolyl]acrylonitrile;
1-(2-nitro-4-chloro-5-methylphenyl)-1-(2-propenyloxy)-2-cyano-4-methyl-4,5-oxido-1-penten-3-one;
N,N-dimethyl-alpha-cyano-beta-benzoyloxy-2-nitro-4-chlorocinnamamide;
Azetidino-alpha-cyano-beta-hydroxy-2-nitro-4-difluoromethoxycinnamamide;
1-(2-nitro-3,5-dimethyl-4-chlorophenyl)-1-oxido-2-cyano-4,4-dimethyl-1-penten-3-one sodium salt;
1-[2-(3-nitro-5-chloro)pyridyl]-1-cyclohexylcarbonyloxy-2-cyano-4,4-dimethyl-1-penten-3-one;
bis[1-(2-nitro-4-chloro-5-methoxyphenyl)-1-oxido-2-cyano-4,4-dimethyl-1-penten-3-one]zinc (II) salt;
1-(2-nitro-4-chloro-5-dimethylaminocarbonyloxyphenyl)-1-dimethylaminocarbonyloxy-2-cyano-4,4-dimethyl-1-penten-3-one;
1-(2-nitro-4-chloro-5-acetyloxyphenyl)-1-hydroxy-2-cyano-4,4-dimethyl-1-penten-3-one;
1-(2-nitro-4-dimethylaminocarbonyloxyphenyl)-1-(4-trifluoromethylbenzoyloxy)-2-cyano-4,4-dimethyl-1-penten-3-one;
1-(2-formamidophenyl)-1-oxido-2-cyano-4,4-dimethyl-1-penten-3-one;
alpha-[3-(1,3-dimethyl)azetidinyl]carbonyl-beta-hydroxy-2-difluoromethoxy-4-chlorocinnamonitrile;
alpha-[3-(N-acetyl-3-methyl)azetidinyl]carbonyl-beta-hydroxy-2-nitro-4-chlorocinnamonitrile;
1-[6-(5-nitro)benzthiazolin-2-onyl]-1-hydroxy-2-cyano-4,4-dimethyl-1-penten-3-one;
1-[6-(5-nitro)benzthiazolyl]-1-hydroxy-2-cyano-4,4-dimethyl-1-penten-3-one;
1-[5-(2-chloro-6-nitro)benzthiazolyl]-1-hydroxy-2-cyano-4,4-dimethyl-1-penten-3-one;
1-(2-nitro-4,5-difluoromethylenedioxyphenyl)-1-hydroxy-2-cyano-4,4-dimethyl-1-penten-3-one;
1-(2-nitro-4,5-carbonyldioxyphenyl)-1-hydroxy-2-cyano-4,4-dimethyl-1-penten-3-one;
1-[5-(6-nitro)benzimidazol-2-onyl]-1-hydroxy-2-cyano-4,4-dimethyl-1-penten-3-one;
1-[6-(7-nitro)quinoxalin-2,3-dionyl]-1-hydroxy-2-cyano-4,4-dimethyl-1-penten-3-one;
1-[2-(3-nitro-5-chloro)thiophenyl]-1-(4-methylphenylsulfonyloxy)-2-cyano-4,4-dimethyl-1-penten-3-one;
1-[5-(2-chloro-4-nitro)thiazolyl]-1-(phenylcarbonylmethoxy)-2-cyano-4,4-dimethyl-1-penten-3-one;
1-[3-(2-nitro-5-chloro)thiophenyl]-1-methoxymethoxy-2-cyano-4,4-dimethyl-1-penten-3-one;
1-[5-(6-nitro)benzisoxazolyl]-1-hydroxy-2-cyano-4,4-dimethyl-1-penten-3-one;
1-[5-(6-nitro)benzpyrazolyl]-1-methoxy-2-cyano-4,4-dimethyl-1-penten-3-one;
1-[5-(4-nitro)benzisothiazolyl]-1-methoxycarbonyloxy-2-cyano-4,4-dimethyl-1-penten-3-one;
1-[7-(1-hydroxy)benztriazolyl]-1-hydroxy-2-cyano-4,4-dimethyl-1-penten-3-one;

N,N-dimethyl-alpha-cyano-beta-benzoyloxy-2-nitro-4-chlorocinnamamide;
Azetidino-alpha-cyano-beta-hydroxy-2-nitro-4-difluoromethoxycinnamamide;
1-(2-nitro-3,5-dimethyl-4-chlorophenyl)-1-oxido-2-cyano-4,4-dimethyl-1-penten-3-one sodium salt;
1-[2-(3-nitro-5-chloro)pyridyl]-1-cyclohexylcarbonyloxy-2-cyano-4,4-dimethyl-1-penten-3-one;
bis[1-(2-nitro-4-chloro-5-methoxyphenyl)-1-oxido-2-cyano-4,4-dimethyl-1-penten-3-one]zinc (II) salt;
1-(2-nitro-4-chloro-5-dimethylaminocarbonyloxyphenyl)-1-dimethylaminocarbonyloxy-2-cyano-4,4-dimethyl-1-penten-3-one;
1-(2-nitro-4-chloro-5-acetyloxyphenyl)-1-hydroxy-2-cyano-4,4-dimethyl-1-penten-3-one;
1-(2-nitro-4-phenoxyphenyl)-1-hydroxy-2-cyano-4,4-dimethyl-1-penten-3one;
1-[2-nitro-4-(4-trifluoromethylphenoxy)phenyl]-1-hydroxy-2-cyano-4,4-dimethyl-1-penten-3-one;
1-[2-nitro-4-(2-chloro-4-trifluoromethylphenoxy)phenyl]-1-hydroxy-2-cyano-4,4-dimethyl-1-penten-3-one;
1-[2-nitro-4-(5-trifluoromethyl-2-pyridyloxy)phenyl]-1-hydroxy-2-cyano-4,4-dimethyl-1-penten-3-one;
1-(2-nitro-4-acetyloxyphenyl)-1-(4-trifluoromethylbenzoyloxy)-2-cyano-4,4-dimethyl-1-penten-3-one;
1-(2-nitro-4-formamidophenyl)-1-oxido-2-cyano-4,4-dimethyl-1-penten-3-one;
1-[6-(5-nitro)benzthiazolin-2-onyl]-1-hydroxy-2-cyano-4,4-dimethyl-1-penten-3-one;
1-[6-(5-nitro)benzthiazolyl]-1-hydroxy-2-cyano-4,4-dimethyl-1-penten-3-one;
1-[5-(2-chloro-6-nitro)benzthiazolyl]-1-hydroxy-2-cyano-4,4-dimethyl-1-penten-3-one;
1-(2-nitro-4,5-difluoromethylenedioxyphenyl)-1-hydroxy-2-cyano-4,4-dimethyl-1-penten-3-one;
1-(2-nitro-4,5-carbonyldioxyphenyl)-1-hydroxy-2-cyano-4,4-dimethyl-1-penten-3-one;
1-[5-(6-nitro)benzimidazol-2-onyl]-1-hydroxy-2-cyano-4,4-dimethyl-1-penten-3-one;
1-[6-(7-nitro)quinoxolin-2,3-dionyl]-1-hydroxy-2-cyano-4,4-dimethyl-1-penten-3-one;
1-[2-(3-nitro-5-chloro)thiophenyl]-1-(4-methylphenylsulfonyloxy)-2-cyano-4,4-dimethyl-1-penten-3-one;
1-[5-(2-chloro-4-nitro)thiazolyl]-1-(phenylcarbonylmethoxy)-2-cyano-4,4-dimethyl-1-penten-3-one;
1-[3-(2-nitro-5-chloro)thiophenyl]-1-methoxymethoxy-2-cyano-4,4-dimethyl-1-penten-3-one;
1-[5-(6-nitro)benzisoxazolyl]-1-hydroxy-2-cyano-4,4-dimethyl-1-penten-3-one;
1-[5-(6-nitro)benzpyrazolyl]-1-methoxy-2-cyano-4,4-dimethyl-1-penten-3-one;
1-[5-(4-nitro)benzisothiazolyl]-1-methoxycarbonyloxy-2-cyano-4,4-dimethyl-1-penten-3-one;
1-[7-(1-hydroxy)benztriazolyl]-1-hydroxy-2-cyano-4,4-dimethyl-1-penten-3-one;
N,N-dimethyl-2-(2-nitro-4-chlorobenzoyl)-2-cyanoacetamide;
N,N-dimethyl-alpha-ethoxy carbonyl-beta-methoxy-2,4-dichlorocinnamamide;
Methyl-alpha-dimethylaminocarbonyl-beta-benzyloxy-2,4-dichlorocinnamate;
Methyl-alpha-dimethylaminocarbonyl-beta-methoxy-2,4-dichlorocinnamate;
Methyl-alpha-dimethylaminocarbonyl-beta-(2,4-dichlorobenzoyloxy)-2,4-dichlorocinnamate;
Ethyl-alpha-dimethylaminocarbonyl-beta-hydroxy-2,4-dichlorocinnamate;
Ethyl-alpha-dimethylaminocarbonyl-beta-benzoyloxy-2,4-dichlorocinnamate;
Ethyl-alpha-dimethylaminocarbonyl-beta-benzoylmethoxy-2,4-dichlorocinnamate;
Ethyl-alpha-dimethylaminocarbonyl-beta-acetoxy-2,4-dichlorocinnamate;
Ethyl-alpha-dimethylaminocarbonyl-beta-hydroxy-2,4-dichlorocinnamate sodium salt;
Ethyl-alpha-dimethylaminocarbonyl-beta-ethoxycarbonyloxy-2,4-dichlorocinnamate;
Ethyl-alpha-dimethylaminocarbonyl-beta-(4-methylphenylsulfonyloxy)-2,4-dichlorocinnamate;
Ethyl-alpha-dimethylaminocarbonyl-beta-diethylaminocarbonyloxy-2,4-dichlorocinnamate;
N,N-dimethyl-alpha-cyano-beta-(2,4-dichlorobenzoyloxy)-2,4-dichlorocinnamamide;
N,N-dimethyl-alpha-cyano-beta-hydroxy-2,4-dichlorocinnamamide;
Methyl-alpha-cyano-beta-(2,4-dichlorobenzoyloxy)-2,4-dichlorocinnamate;
Ethyl-alpha-methylcarbonyl-beta-(2,4-dichlorobenzoyloxy)-2,4-dichlorocinnamate;
Methyl-alpha-cyano-beta-hydroxy-2,4-dichlorocinnamate;
Ethyl-alpha-methylcarbonyl-beta-hydroxy-2,4-dichlorocinnamate;
1-(2,4-dichlorophenyl)-1-(2,4-dichlorobenzoyloxy)-2-methylcarbonyl-1-buten-3-one;
1-(2,4-dichlorophenyl)-1-hydroxy-2-methylcarbonyl-1-buten-3-one;
1-(2,4-dichlorophenyl)-1-(2,4-dichlorobenzoyloxy)-2-methylsulfonyl-1-buten-3-one;
Piperidino-alpha-ethoxycarbonyl-beta-(2,4-dichlorobenzoyloxy)-2,4-dichlorocinnamamide;
Pyrrolidino-beta-ethoxycarbonyl-beta-(2,4-dichlorobenzoyloxy)-2,4-cinnamamide;
Piperidino-alpha-ethoxycarbonyl-beta-hydroxy-2,4-dichlorocinnamamide;
Morpholino-alpha-ethoxycarbonyl-beta-(2,4-dichlorobenzoyloxy)-2,4-dichlorocinnamamide;
Pyrrolidino-alpha-ethoxycarbonyl-beta-hydroxy-2,4-dichlorocinammamide;
Morpholino-alpha-ethoxycarbonyl-beta-hydroxy-2,4-dichlorocinnamamide;
N,N-dimethyl-alpha-methylcarbonyl-beta-hydroxy-2,4-dichlorocinnamamide;
N,N-dimethyl-alpha-methylcarbonyl-beta-(2,4-dichlorobenzoyloxy)-2,4-dichlorocinnamamide;
N,N-dimethyl-alpha-cyano-beta-benzoyloxycinnamamide;
N,N-dimethyl-alpha-cyano-beta-hydroxycinnamamide;
N,N-dimethyl-alpha-cyano-beta-hydroxy-2-chlorocinnamamide;
N,N-dimethyl-alpha-cyano-beta-(2-chlorobenzoyloxy)-2-chlorocinnamamide;
N,N-dimethyl-alpha-cyano-beta-(2,6-dichlorobenzoyloxy)-2,6-dichlorocinnamamide;
N,N-dimethyl-alpha-cyano-beta-hydroxy-2-methoxycinnamamide;
N,N-dimethyl-alpha-cyano-beta-(2,3,6-trichlorobenzoyloxy)-2,3,6-trichlorocinnamamide;
N,N-dimethyl-alpha-cyano-beta-(2,5-dichlorobenzoyloxy)-2,5-dichlorocinnamamide;
N,N-dimethyl-alpha-cyano-beta-(2-nitrobenzoyloxy)-2-nitrocinnamamide;
N,N-dimethyl-alpha-cyano-beta-hydroxy-2,6-dichlorocinnamamide;

N,N-dimethyl-alpha-cyano-beta-hydroxy-2,3,5-trichlorocinnamamide;
N,N-dimethyl-alpha-cyano-beta-hydroxy-2-nitrocinnamide;
N,N-dimethyl-alpha-cyano-beta-hydroxy-2,5-dichlorocinnamamide;
N,N-dimethyl-alpha-cyano-beta-(2-nitro-5-methylbenzoyloxy)-2-nitro-5-methylcinnamamide;
N,N-dimethyl-alpha-cyano-beta-hydroxy-2-nitro-5-methylcinnamamide;
N,N-dimethyl-alpha-cyano-beta-hydroxy-2-nitro-3-methylcinnamamide;
N,N-dimethyl-alpha-cyano-beta-(2-trifluoromethylbenzoyloxy)-2-trifluoromethylcinnamamide;
N,N-dimethyl-alpha-cyano-beta-hydroxy-2-trifluoromethylcinnamamide;
N,N-dimethyl-alpha-cyano-beta-(2-nitro-4-chlorobenzoyloxy)-2-nitro-4-chlorocinnamamide;
N,N-dimethyl-alpha-cyano-beta-hydroxy-2-nitro-4-chlorocinnamamide;
N,N-dimethyl-alpha-cyano-beta-hydroxy-2,4-dinitrocinnamamide;
N,N-dimethyl-alpha-cyano-beta-hydroxy-2-nitro-6-methylcinnamamide;
N,N-dimethyl-alpha-cyano-beta-hydroxy-2-chloro-4-nitrocinnamamide;
N,N-dimethyl-alpha-cyano-beta-hydroxy-2-nitro-6-chlorocinnamamide;
N,N-dimethyl-alpha-cyano-beta-hydroxy-2-nitro-4-fluorocinnamamide;
N,N-dimethyl-alpha-cyano-beta-hydroxy-2-ioddocinnamamide;
N,N-dimethyl-alpha-cyano-beta-hydroxy-2-nitro-4-methoxycinnamamide;
Morpholino-alpha-cyano-beta-hydroxy-2-nitro-4-chlorocinnamamide;
1-(2-nitro-4-chlorophenyl)-1-hydroxy-2-cyano-4-methyl-1-penten-3-one;
Methyl-alpha-cyano-beta-hydroxy-2-nitro-4-chlorocinnamate;
Piperidino-alpha-cyano-beta-hydroxy-2-nitro-4-chlorocinnamamide;
1-(2-nitro-4-chlorophenyl)-1-hydroxy-2-cyano-1-penten-3-one;
2-cyano-3-hydroxy-3-(2-nitro-4-chlorophenyl)-acrylophenone;
N,N-dimethyl-alpha-cyano-beta-oxido-2-nitro-4-chlorocinnamamide sodium salt;
N,N-dimethyl-alpha-cyano-beta-hydroxy-2-methoxycarbonylcinnamamide;
iso-propyl-alpha-cyano-beta-hydroxy-2-nitro-4-chlorocinnamate;
N,N-dimethyl-alpha-cyano-beta-hydroxy-2-methylsulfonylcinnamamide;
N,N-dimethyl-alpha-cyano-beta-hydroxy-2-nitro-4-trifluoromethylcinnamamide;
1-(2,4-dichlorophenyl)-1-hydroxy-2-(2-propylcarbonyl)-4-methyl-1-penten-3-one;
1-(2,4-dichlorophenyl)-1-hydroxy-2-cyano-4,4-dimethyl-1-penten-3-one;
1-(2-nitro-4-chlorophenyl)-1-hydroxy-2-cyano-4,4-dimethyl-1-penten-3-one;
1-(2-nitro-4-chlorophenyl)-1-hydroxy-2-cyano-4-methyl-1-hexen-3-one;
Ethyl-alpha-methylcarbonyl-beta-hydroxy-2,4-dichlorocinnamate sodium salt;
Ethyl-alpha-(2-propylcarbonyl)-beta-hydroxy-2,4-dichlorocinnamate;
1-(2,4-dichlorophenyl)-1-hydroxy-2-cyano-4-methyl-1-penten-3-one;
bis[1-(2,4-dichlorophenyl)-1-oxido-2-cyano-4,4-dimethyl-1-penten-3-one]magnesium salt;
bis[1-(2-nitro-4-chlorophenyl)-1-oxido-2-cyano-4,4-dimethyl-1-penten-3-one]magnesium salt;
bis[1-(2-nitro-4-chlorophenyl)-1-oxido-2-cyano-4-methyl-1-hexen-3-one]magnesium salt;
N,N-dimethyl-alpha-cyano-beta-oxido-2-aminocarbonylcinnamamide ammonium salt;
N,N-dimethyl-alpha-cyano-beta-(2-methyl-4-chlorobenzoyloxy)-2-methyl-4-chlorocinnamamide;
N,N-dimethyl-alpha-cyano-beta-hydroxy-2-methyl-4-chlorocinnamamide;
N,N-dimethyl-alpha-cyano-beta-hydroxy-2-cyanocinnamamide;
1-(2-nitro-4-chlorophenyl)-1-hydroxy-2-cyano-5-methyl-1-hexen-3-one;
N,N-dimethyl-alpha-cyano-beta-hydroxy-2,3,5-trichlorocinnamamide;
1-(2,4-dichlorophenyl)-1-hydroxy-2-bromo-4-methyl-1-penten-3-one;
1-(2-nitro-4-chlorophenyl)-1-hydroxy-2-cyano-4,4-dimethyl-1-hexen-3-one;
2-bromo-2-(2-nitro-4-chlorophenylcarbonyl)-2-(2-propylcarbonyl)acetonitrile;
N,N-dimethyl-2-cyano-3-hydroxy-3-(2-furanyl)acrylamide;
N,N-dimethyl-alpha-cyano-beta-(2-nitro-4-methylbenzoyloxy)-2-nitro-4-methylcinnamamide;
N,N-diethyl-alpha-cyano-beta-hydroxy-2-nitro-4-chlorocinnamamide;
N,N-dimethyl-alpha-cyano-beta-hydroxy-2-nitro-4-methylcinnamamide;
N,N-dimethyl-2-cyano-3-hydroxy-3-[2-(5-nitrofuranyl)]acrylamide;
1-(2,4-dichlorophenyl)-2-chloro-4-methyl-1,3-dioxopentane;
1-(2,4-dichlorophenyl)-2-chloro-4,4-dimethyl-1,3-dioxopentane;
N,N-dimethyl-alpha-cyano-beta-hydroxy-2-nitro-4-bromocinnamamide;
1-(2-nitro-4-chlorophenyl-1-hydroxy-2-cyano-4-methyl-1-penten-3-one complexed to Ambersep ®900 (hydroxide form);
1-(2-nitro-4-trifluoromethylphenyl)-1-hydroxy-2-cyano-4-methyl-1-penten-3-one;
1-(2-nitro-4-chlorophenyl)-1-hydroxy-2-methylcarbonyl-4,4-dimethyl-1-penten-3-one;
1-(2,4-dichlorophenyl)-1-hydroxy-2-methylcarbonyl-4,4-dimethyl-1-penten-3-one;
N,N-dimethyl-2-cyano-3-hydroxy-3-[2-(5-chlorothiophenyl)]acrylamide;
1-(2-nitro-4-chlorophenyl)-1-oxido-2-cyano-4,4-dimethyl-1-penten-3-one potassium salt;
1-(2-nitro-4-chlorophenyl)-1-oxido-2-cyano-4,4-dimethyl-1-penten-3-one lithium salt;
1-(2-nitro-4-chlorophenyl)-1-benzoyloxy-2-cyano-4-methyl-1-penten-3-one;
1-(2-nitro-4-chlorophenyl)-1-methoxy-2-cyano-4,4-dimethyl-1-penten-3-one+other methyl enol ether isomers;
1-(2,4-dichlorophenyl)-1-hydroxy-2-methylthio-4-methyl-1-penten-3-one;
1-(2-nitro-4-chlorophenyl)-1-hydroxy-2-cyano-4,4-dimethyl-1-penten-3-one complexed to Ambersep ®900 (hydroxide form);

bis[1-(2-nitro-4-chlorophenyl)-1-oxido-2-cyano-4-methyl-1-penten-3-one]copper (II) salt;
bis[1-(2-nitro-4-chlorophenyl)-1-oxido-2-cyano-4,4-dimethyl-1-penten-3-one]copper (II) salt;
1-(2-nitro-4-chlorophenyl)-1-hydroxy-2-cyano-4,4-dimethyl-1-penten-3-one complexed to a strong base (hydroxide form) polystyrene macroreticular ultrafine resin;
1-(2-nitro-4-chlorophenyl)-1-hydroxy-2-cyano-4,4-dimethyl-1-penten-3-one complexed to a weak base polystyrene macroreticular ultrafine resin;
1-(2-nitro-4-trifluoromethylphenyl)-1-hydroxy-2-cyano-4,4-dimethyl-1-penten-3-one;
1-(2-nitro-4-chlorophenyl)-1-hydroxy-2-cyano-4,4-dimethyl-5-chloro-1-penten-3-one;
1-(2,4-dichlorophenyl)-1-hydroxy-2-cyano-4,4-dimethyl-5-chloro-1-penten-3-one;
1-(2-nitro-4-chloro-5-methoxycarbonylphenyl)-1-hydroxy-2-cyano-4,4-dimethyl-1-penten-3-one;
1-(2-nitro-4-chloro-5-dimethylaminophenyl)-1-hydroxy-2-cyano-4,4-dimethyl-1-penten-3-one;
1-(2-nitro-4-difluoromethoxyphenyl)-1-hydroxy-2-cyano-4,4-dimethyl-1-penten-3-one;
1-(2-nitro-4-trifluoromethoxyphenyl)-1-hydroxy-2-cyano-4,4-dimethyl-1-penten-3-one;
1-(2-nitro-4-chlorodifluoromethoxyphenyl)-1-hydroxy-2-cyano-4,4-dimethyl-1-penten-3-one;
1-(2-nitro-4-cyanophenyl)-1-hydroxy-2-cyano-4,4-dimethyl-1-penten-3-one;
1-(2-nitro-4-chlorophenyl)-1-acetoxy-2-cyano-4,4-dimethyl-1-penten-3-one;
1-(2-nitro-4-chlorophenyl)-1-benzoyloxy-2-cyano-4,4-dimethyl-1-penten-3-one;
1-(2-nitro-4-chlorophenyl)-1-(2-methylbenzoyloxy)-2-cyano-4,4-dimethyl-1-penten-3-one;
1-(2-nitro-4-chlorophenyl)-1-(4-trifluoromethylbenzoyloxy)-2-cyano-4,4-dimethyl-1-penten-3-one;
1-(2-trifluoromethylphenyl)-1-hydroxy-2-cyano-4,4-dimethyl-1-penten-3-one;
1-(2-trifluoromethyl-4-chlorophenyl)-1-hydroxy-2-cyano-4,4-dimethyl-1-penten-3-one;
1-(2-nitro-4-chlorophenyl)-1-(4-chlorobenzoyloxy)-2-cyano-4,4-dimethyl-1-penten-3-one;
1-(2-nitro-4-chlorophenyl)-1-(methoxycarbonylmethoxy)-2-cyano-4,4-dimethyl-1-penten-3-one;
1-(2-nitro-4-chlorophenyl)-1-benzyloxy-2-cyano-4,4-dimethyl-1-penten-3-one;
1-(2-nitro-4-chlorophenyl)-1-methoxycarbonyloxy-2-cyano-4,4-dimethyl-1-penten-3-one;
1-(2-nitro-4-chlorophenyl)-1-dimethylaminocarbonyloxy-2-cyano-4,4-dimethyl-1-penten-3-one;
1-(2-nitro-4-chlorophenyl)-1-hydroxy-2-cyano-4,5-oxido-4-methyl-1-penten-3-one;
1-(2-nitro-4-chlorophenyl)-1-hydroxy-2-cyano-4-fluoro-4-methyl-1-penten-3-one;
1-(2-nitro-4-chlorophenyl)-1-hydroxy-2-cyano-4-chloro-4-methyl-1-penten-3-one;
1-(2-nitro-4-chlorophenyl)-1-hydroxy-2-cyano-4-cyano-4-methyl-1-penten-3-one;
1-(2-nitro-4-chlorophenyl)-1-hydroxy-2-cyano-4-hydroxy-4-methyl-1-penten-3-one;
1-(2-nitro-4-chlorophenyl)-1-hydroxy-2-cyano-4,4-difluoro-1-penten-3-one;
1-(2-nitro-4-chlorophenyl)-1-hydroxy-2-cyano-4,4-dichloro-1-penten-3-one;
1-(2-nitro-4-chlorophenyl)-1-hydroxy-2-cyano-4-methoxy-4-methyl-1-penten-3-one;
1-(2-nitro-4-chlorophenyl)-1-hydroxy-2-cyano-4-bromo-4-methyl-1-penten-3-one;
1-(2-nitro-4-chlorophenyl)-1-hydroxy-2-cyano-4,4,4-trichloro-1-penten-3-one;
1-(2-nitro-4-chlorophenyl)-1-hydroxy-2-cyano-4,4,4-trifluoro-1-penten-3-one;
alpha-cyclopropylcarbonyl-beta-hydroxy-2-nitro-4-chlorocinnamonitrile;
alpha-(1-methylcyclopropyl)carbonyl-beta-hydroxy-2-nitro-4-chlorocinnamonitrile;
alpha-(1-methylcyclobutyl)carbonyl-beta-hydroxy-2-nitro-4-chlorocinnamonitrile;
alpha-(3-methyloxetanyl)carbonyl-beta-hydroxy-2-nitro-4-chlorocinnamonitrile;
1-[2-(5-chloro)pyridyl]-1-hydroxy-2-cyano-4,4-dimethyl-1-penten-3-one;
1-(8-quinolinyl)-1-hydroxy-2-cyano-4,4-dimethyl-1-penten-3-one;
1-(8-quinolinyl)-1-hydroxy-2-cyano-4,4-dimethyl-1-penten-3-one N-oxide;
1-[4-(3-nitro)pyridyl]-1-hydroxy-2-cyano-4,4-dimethyl-1-penten-3-one;
1-[6-(7-nitro)quinolinyl]-1-hydroxy-2-cyano-4,4-dimethyl-1-penten-3-one;
1-[6-(5-nitro)quinolinyl]-1-hydroxy-2-cyano-4,4-dimethyl-1-penten-3-one;
1-[6-(7-nitro)isoquinolinyl]-1-hydroxy-2-cyano-4,4-dimethyl-1-penten-3-one;
1-[6-(5-nitro)isoquinolinyl]-1-hydroxy-2-cyano-4,4-dimethyl-1-penten-3-one;
1-(2-nitro-4-chloro-5-methylphenyl)-1-hydroxy-2-cyano-4,4-dimethyl-1-penten-3-one;
1-(2-nitro-3-methyl-4-chlorophenyl)-1-hydroxy-2-cyano-4,4-dimethyl-1-penten-3-one; and
1-(2-nitro-3,5-dimethyl-4-chlorophenyl)-1-hydroxy-2-cyano-4,4-dimethyl-1-penten-3-one;
1-(2-trifluoromethyl-4-chlorophenyl)-1-hydroxy-2-cyano-4,4-dimethyl-1-penten-3-one;
1-(2-trifluoromethyl-4-bromophenyl)-1-hydroxy-2-cyano-4,4-dimethyl-1-penten-3-one;
1-(2-trifluoromethyl-4-pentafluoroethyl-phenyl)-1-hydroxy-2-cyano-4,4-dimethyl-1-penten-3-one;
1-(2,4-bistrifluoromethylphenyl)-1-hydroxy-2-cyano-4,4-dimethyl-1-penten-3-one;
1-(2-trifluoromethyl-4-trifluoromethoxyphenyl)-1-hydroxy-2-cyano-4,4-dimethyl-1-penten-3-one;
1-(2-trifluoromethyl-4-difluoromethoxyphenyl)-1-hydroxy-2-cyano-4,4-dimethyl-1-penten-3-one;
1-(2-trifluoromethyl-4-ethoxyphenyl)-1-hydroxy-2-cyano-4,4-dimethyl-1-penten-3-one;
1-(2-trifluoromethyl-4-phenoxyphenyl)-1-hydroxy-2-cyano-4,4-dimethyl-1-penten-3-one;
1-(2-trifluoromethyl-4-(2,2,2-trifluoroethoxy)phenyl)-1-hydroxy-2-cyano-4,4-dimethyl-1-penten-3-one;
1-(2-difluoromethoxy-4-trifluoromethylphenyl)-1-hydroxy-2-cyano-4,4-dimethyl-1-penten-3-one;
1-(2-fluoromethyl-4-trifluoromethylphenyl)-1-hydroxy-2-cyano-4,4-dimethyl-1-penten-3-one;
1-(2-difluoromethyl-4-trifluoromethylphenyl)-1-hydroxy-2-cyano-4,4-dimethyl-1-penten-3-one;
1-(2-1,1-difluoroethyl)-4-trifluoromethylphenyl-1-hydroxy-2-cyano-4,4-dimethyl-1-penten-3-one;
1-(2-nitro-4-tert-butylphenyl)-1-hydroxy-2-cyano-4,4-dimethyl-1-penten-3-one;
1-(2-trifluoromethyl-4-n-pentylphenyl)-1-hydroxy-2-cyano-4,4-dimethyl-1-penten-3-one;
1-(2-nitro-4-n-pentylphenyl)-1-hydroxy-2-cyano-4,4-dimethyl-1-penten-3-one;

1-(2-nitro-4-(3-trifluoromethylphenoxyphenyl)-1-hydroxy-2-cyano-4,4-dimethyl-1-penten-3-one;

1-(2-nitro-4-(4-chlorophenoxy)phenyl)-1-hydroxy-2-cyano-4,4-dimethyl-1-penten-3-one;

1-(2-nitro-4-(2-methylphenoxy)phenyl)-1-hydroxy-2-cyano-4,4-dimethyl-1-penten-3-one;

1-(2-trifluoromethyl-4-(3-trifluoromethylphenoxy)phenyl)-1-hydroxy-2-cyano-4,4-dimethyl-1-penten-3-one;

1-(2-trifluoromethyl-4-(2-methylphenoxy)phenyl)-1-hydroxy-2-cyano-4,4-dimethyl-1-penten-3-one;

1-(2-trifluoromethyl-4-trifluoromethylthiophenyl)-1-hydroxy-2-cyano-4,4-dimethyl-1-penten-3-one;

1-(2-nitro-4-trifluoromethylthiophenyl)-1-hydroxy-2-cyano-4,4-dimethyl-1-penten-3-one;

1-(2-nitro-4-thioethoxyphenyl)-1-hydroxy-2-cyano-4,4-dimethyl-1-penten-3-one;

1-(2-trifluoromethyl-4-thioethoxyphenyl)-1-hydroxy-2-cyano-4,4-dimethyl-1-penten-3-one.

1-(2-nitro-4-fluorophenyl)-1-hydroxy-2-cyano-4,4-dimethyl-1-penten-3-one;

1-(2-nitro-4-difluoromethoxyphenyl)-1-hydroxy-2-cyano-4,4-dimethyl-1-penten-3-one;

1-(2-nitro-4-cyanophenyl)-1-hydroxy-2-cyano-4,4-dimethyl-1-penten-3-one;

1-(2,4-dinitrophenyl)-1-hydroxy-2-cyano-4,4-dimethyl-1-penten-3-one;

1-(2-nitro-4-n-propoxyphenyl)-1-hydroxy-2-cyano-4,4-dimethyl-1-penten-3-one;

1-(2-nitro-4-chlorophenyl)-1-hydroxy-2-cyano-3-[1-(1-methylcyclopropyl)]-1-propen-3-one;

1-(2-nitro-4-tetrafluoroethoxyphenyl)-1-hydroxy-2-cyano-4,4-dimethyl-1-penten-3-one.

Because of their herbicidal activity, preferred compounds of the present invention include those of Formula I where, independently:

A is $COR^1$; $CONR^4R^5$ or $R^4$ and $R^5$ can be joined together with the nitrogen to which they are attached to form a heterocycle containing from 3 to 6 nuclear carbon atoms and from 1 to 2 additional letter atoms selected from nitrogen or oxygen;

B is cyano or $CO_2R$;

V is hydrogen, $(C_1-C_6)$alkyl or $COR^3$;

W is

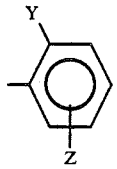

where

Y is halo, nitro or $(C_1-C_4)$haloalkyl; and

Z is from one to three of the same or different halo, $(C_1-C_6)$haloalkyl or $(C_1-C_6)$haloalkoxy;

R is $(C_1-C_4)$alkyl;

$R^1$ is $(C_1-C_4)$alkyl;

$R^3$ is $(C_1-C_6)$alkyl or unsubstituted or substituted phenyl having one to three of the same or different halo, nitro, cyano, $(C_1-C_4)$alkyl, $(C_1-C_4)$alkoxy, $(C_1-C_4)$haloalkyl, carboxy, $(C_1-C_4)$alkanoyloxy or $(C_1-C_4)$alkoxycarbonyl; and $R^4$ and $R^5$ are, independently, $(C_1-C_3)$alkyl; and agronomically acceptable salts thereof.

Because of their herbicidal activity, most preferred compounds of the present invention include those of Formula I wherein independently:

A is $COR^1$;

B is cyano;

V is hydrogen;

W is

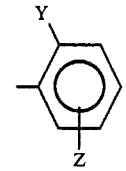

where

Y is nitro or $(C_1-C_4)$haloalkyl; and

Z is from one to two of the same or different halo, $(C_1-C_6)$haloalkyl, or $(C_1-C_6)$haloalkoxy;

$R^1$ is $(C_1-C_4)$branched alkyl;

and agronomically acceptable salts thereof.

The enols of the present invention, or their precursors, are prepared by reacting a compound of the following formula:

where A and B are as defined above for Formula I, in the presence of a base and a solvent or solvent mixture with a compound of the following formula

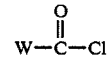

where W is as defined above for Formula I.

Examples of suitable bases for the above reaction include trialkylamines, such as triethylamine, alkaline earth carbonates, such as $K_2CO_3$, metal hydrides such as LiH, NaH, metal alkoxides such as $Mg(OCH_2CH_3)_2$, and the like. Examples of suitable solvents, or mixtures thereof, include ethers, such as tetrahydrofuran (THF) and glyme, hydrocarbons, such as toluene, acetonitrile, N,N-dialkylamides, such as dimethylformamide, and halocarbons, such as methylene dichloride. This reaction is generally carried out at a temperature of from about $-10°$ C. to about $100°$ C. and preferably the temperatures employed are in the range of from about $0°$ C. to about $70°$ C.

The salts of the invention can be prepared by any convenient art-recognized method, such as by reacting a metal hydroxide, a metal hydride, a trialkylsulfonium halide, a trialkylsulfoxonium halide, a tetraalkylphosphonium halide, or an amine or ammonium salt, such as a halide, hydroxide or alkoxide with the free acid, or reacting a quarternary ammonium salt, such as a chloride, a bromide, nitrate or the like with a metal salt of the invention in a suitable solvent. When metal hydroxides are used as reagents, useful solvents include water, glyme, dioxane, tetrahydrofuran, methanol, ethanol, isopropanol and the like. When metal hydrides are used as reagents, useful solvents include nonhydroxylic solvents such as dioxane, glyme, tetrahydrofuran, diethyl ether, hydrocarbons such as toluene, xylene, hexane, pentane, heptane, and octane, dimethylformamide, and the like. When trialkylsulfonium halides or trialkylsulfoxonium halides are used as reagents, useful solvents include water, diethyl ether, dimethoxymethane, dioxane, tetrahydrofuran, ethanol, dimethyl sulfoxide (DMSO), dimethyl formamide (DMF) and acetonitrile. Preferably this reaction is carried out in the presence of an acid scavenger such as propylene oxide. When tetraalkylphosphonium halides are used as reagents, useful solvents include water, acetone, ethanol and tetrahydrofuran. Preferably this reaction is carried out in the presence of an acid scavenger such as propylene oxide. When amines are used as reagents, useful solvents include alcohols, such as methanol or ethanol, hydrocarbons, such as toluene, xylene, hexane and the like, tetrahydrofuran, glyme, dioxane, or water. When ammonium salts are used as reagents, useful solvents include water, alcohols, such as methanol or ethanol, glyme, tetrahydrofuran, or the like. When the ammonium salt is other than a hydroxide or alkoxide, an additional base, such as potassium or sodium hydroxide, hydride, or alkoxide is generally used. The particular choice of solvent will depend on the relative solubilities of the starting materials and the resultant salts, and slurries rather than solutions of certain reagents may be used to obtain the salts. Generally, equivalent amounts of the starting reagents are used and the salt-forming reaction is carried out at about 0° C. to about 100° C., preferably at about room temperature.

The salts of the present invention can also be prepared by reacting the free acid with a suitably loaded cationic exchange resin. Preferably, a polystyrene macroreticular ultrafine resin (PMR) is used. Either a weak base or strong base (hydroxide form) may be used and is ground to an average particle size of about one micron. The exchange resin can be loaded with the desired agronomically acceptable alkali metal cation such as sodium, potassium, lithium or the like, an alkaline earth metal cation such as calcium, magnesium, barium, strontium or the like, a heavy metal cation such as zinc, manganese, cupric, cuprous, ferric, ferrous, titanium or the like, sulfonium, phosphonium, ammonium, or a primary, secondary, tertiary or quaternary ammonium. These reactions are usually conducted in a suitable solvent such as water, dioxane, tetrahydrofuran, methanol, ethanol, hexane, toluene, xylene or the like. The particular choice of solvent will depend on the relative solubilities of the starting materials and the resulting salts. Generally, equivalent amounts of reagents are used and the reaction is carried out at about 0° C. to about 100° C., preferably at about room temperature.

The following examples will further illustrate this invention but are not intended to limit it in any way. In Table I, typical enols of the present invention are listed. Structures were confirmed by NMR and in most cases by elemental analysis. After Table I, preparation of representative intermediates or precursors are described as Examples A through D. Following Example D, specific illustrative preparation of the compounds of Examples 25, 26, 28, 39, 44, bromine addition product of Example 55, 69, 71, 74, 77, 89, 94, 96, 98, 99, 100, 101, 104, 106, 107 and 108 are described.

TABLE I

| Example No. | A | B | V | W |
|---|---|---|---|---|
| 1 | $-CON(CH_3)_2$ | $-CO_2CH_2CH_3$ | H | $-C_6H_3Cl_2-2,4$ |
| 2 | $-CON(CH_3)_2$ | $-CN$ | H | $-C_6H_3Cl_2-2,4$ |
| 3 | $-CON(CH_3)_2$ | $-COCH_3$ | H | $-C_6H_3Cl_2-2,4$ |
| 4 | $-CON$(piperidinyl) | $-CO_2CH_2CH_3$ | H | $-C_6H_3Cl_2-2,4$ |
| 5 | $-CON$(morpholinyl) | $-CO_2CH_2CH_3$ | H | $-C_6H_3Cl_2-2,4$ |
| 6 | $-CON$(pyrrolidinyl) | $-CO_2CH_2CH_3$ | H | $-C_6H_3Cl_2-2,4$ |
| 7 | $-CO_2CH_2CH_3$ | $-CO_2CH_2CH_3$ | H | $-C_6H_3Cl_2-2,4$ |
| 8 | $-COCH_3$ | $-CO_2CH_2CH_3$ | H | $-C_6H_3Cl_2-2,4$ |
| 9 | $-COCH_3$ | $-COCH_3$ | H | $-C_6H_3Cl_2-2,4$ |
| 10 | $-COCH_3$ | $-SO_2CH_3$ | H | $-C_6H_3Cl_2-2,4$ |
| 11 | $-COCH(CH_3)_2$ | $-CO_2CH_2CH_3$ | H | $-C_6H_3Cl_2-2,4$ |
| 12 | $-COC(CH_3)_3$ | $-CN$ | H | $-C_6H_3Cl_2-2,4$ |
| 13 | $-COCH(CH_3)_2$ | $-CN$ | H | $-C_6H_3Cl_2-2,4$ |
| 14 | $-COCH(CH_3)_2$ | $-COCH(CH_3)_2$ | H | $-C_6H_3Cl_2-2,4$ |
| 15 | $-CON(CH_3)_2$ | $-CO_2CH_2CH_3$ | $-COC_6H_3Cl_2-2,4$ | $-C_6H_3Cl_2-2,4$ |
| 16 | $-CON(CH_3)_2$ | $-CN$ | $-COC_6H_3Cl_2-2,4$ | $-C_6H_3Cl_2-2,4$ |
| 17 | $-CON(CH_3)_2$ | $-COCH_3$ | $-COC_6H_3Cl_2-2,4$ | $-C_6H_3Cl_2-2,4$ |
| 18 | $-CON$(piperidinyl) | $-CO_2CH_2CH_3$ | $-COC_6H_3Cl_2-2,4$ | $-C_6H_3Cl_2-2,4$ |

TABLE I-continued

| Example No. | A | B | V | W |
|---|---|---|---|---|
| 19 | —CON(morpholine) | —CO$_2$CH$_2$CH$_3$ | —COC$_6$H$_3$Cl$_2$—2,4 | —C$_6$H$_3$Cl$_2$—2,4 |
| 20 | —CON(piperidine) | —CO$_2$CH$_2$CH$_3$ | —COC$_6$H$_3$Cl$_2$—2,4 | —C$_6$H$_3$Cl$_2$—2,4 |
| 21 | —COCH$_3$ | —CO$_2$CH$_2$CH$_3$ | —COC$_6$H$_3$Cl$_2$—2,4 | —C$_6$H$_3$Cl$_2$—2,4 |
| 22 | —COCH$_3$ | —COCH$_3$ | —COC$_6$H$_3$Cl$_2$—2,4 | —C$_6$H$_3$Cl$_2$—2,4 |
| 23 | —CO$_2$CH$_2$CH$_3$ | —CO$_2$CH$_2$CH$_3$ | —COC$_6$H$_3$Cl$_2$—2,4 | —C$_6$H$_3$Cl$_2$—2,4 |
| 24 | —CON(CH$_3$)$_2$ | —CO$_2$CH$_2$CH$_3$ | Na$^\oplus$ | —C$_6$H$_3$Cl$_2$—2,4 |
| 25 | —CON(CH$_3$)$_2$ | —CO$_2$CH$_2$CH$_3$ | —CH$_3$ | —C$_6$H$_3$Cl$_2$—2,4 |
| 26 | —CON(CH$_3$)$_2$ | —CO$_2$CH$_2$CH$_3$ | —CH$_2$C$_6$H$_5$ | —C$_6$H$_3$Cl$_2$—2,4 |
| 27 | —CON(CH$_3$)$_2$ | —CO$_2$CH$_2$CH$_3$ | —COCH$_3$ | —C$_6$H$_3$Cl$_2$—2,4 |
| 28 | —CON(CH$_3$)$_2$ | —CO$_2$CH$_2$CH$_3$ | —COC$_6$H$_5$ | —C$_6$H$_3$Cl$_2$—2,4 |
| 29 | —CON(CH$_3$)$_2$ | —CO$_2$CH$_2$CH$_3$ | —COC$_6$H$_3$Cl$_2$—2,4 | —C$_6$H$_3$Cl$_2$—2,4 |
| 30 | —CON(CH$_3$)$_2$ | —CO$_2$CH$_2$CH$_3$ | —CO$_2$CH$_2$CH$_3$ | —C$_6$H$_3$Cl$_2$—2,4 |
| 31 | —CON(CH$_3$)$_2$ | —CO$_2$CH$_2$CH$_3$ | —CON(CH$_3$)$_2$ | —C$_6$H$_3$Cl$_2$—2,4 |
| 32 | —CON(CH$_3$)$_2$ | —CN | H | —C$_6$H$_4$Cl—2 |
| 33 | —CON(CH$_3$)$_2$ | —CN | H | —C$_6$H$_3$Cl$_2$—2,5 |
| 34 | —CON(CH$_3$)$_2$ | —CN | H | —C$_6$H$_3$Cl$_2$—2,6 |
| 35 | —CON(CH$_3$)$_2$ | —CN | H | —C$_6$H$_2$Cl$_3$—2,3,6 |
| 36 | —CON(CH$_3$)$_2$ | —CN | H | —C$_6$H$_4$OCH$_3$—2 |
| 37 | —CON(CH$_3$)$_2$ | —CN | H | —C$_6$H$_4$NO$_2$—2 |
| 38 | —CON(CH$_3$)$_2$ | —CN | H | —C$_6$H$_4$CF$_3$—2 |
| 39 | —CON(CH$_3$)$_2$ | —CN | H | —C$_6$H$_3$NO$_2$—2-Cl—4 |
| 40 | —CON(CH$_3$)$_2$ | —CN | H | —C$_6$H$_3$NO$_2$—2-CH$_3$—3 |
| 41 | —CON(CH$_3$)$_2$ | —CN | H | —C$_6$H$_3$NO$_2$—2-CH$_3$—5 |
| 42 | —CON(CH$_3$)$_2$ | —CN | H | —C$_6$H$_4$NO$_2$—2-Cl—5 |
| 43 | —CON(CH$_3$)$_2$ | —CN | H | —C$_6$H$_3$(NO$_2$)$_2$—2,4 |
| 44 | —CON(CH$_3$)$_2$ | —CN | H | —C$_6$H$_3$NO$_2$—2-CF$_3$—4 |
| 45 | —CON(CH$_3$)$_2$ | —CN | —COC$_6$H$_4$Cl—2 | —C$_6$H$_4$Cl—2 |
| 46 | —CON(CH$_3$)$_2$ | —CN | —COC$_6$H$_4$OCH$_3$—2 | —C$_6$H$_4$OCH$_3$—2 |
| 47 | —CON(CH$_3$)$_2$ | —CN | —COC$_6$H$_3$Cl$_2$—2,5 | —C$_6$H$_3$Cl$_2$—2,5 |
| 48 | —CON(CH$_3$)$_2$ | —CN | —COC$_6$H$_3$Cl$_2$—2,6 | —C$_6$H$_3$Cl$_2$—2,6 |
| 49 | —CON(CH$_3$)$_2$ | —CN | —COC$_6$H$_2$Cl$_3$—2,3,6 | —C$_6$H$_2$Cl$_3$—2,3,6 |
| 50 | —CON(CH$_3$)$_2$ | —CN | —COC$_6$H$_4$NO$_2$—2 | —C$_6$H$_4$NO$_2$—2 |
| 51 | —CON(CH$_3$)$_2$ | —CN | —COC$_6$H$_3$NO$_2$—2-CH$_3$—5 | —C$_6$H$_3$NO$_2$—2-CH$_3$—5 |
| 52 | —CON(CH$_3$)$_2$ | —CN | —COC$_6$H$_3$NO$_2$—2-Cl—5 | —C$_6$H$_3$NO$_2$—2-Cl—5 |
| 53 | —CON(CH$_3$)$_2$ | —CN | —COC$_6$H$_4$CF$_3$—2 | —C$_6$H$_4$CF$_3$—2 |
| 54 | —CON(CH$_3$)$_2$ | —CN | —COC$_6$H$_3$NO$_2$—2-Cl—4 | —C$_6$H$_3$NO$_2$—2-Cl—4 |
| 55 | —COCH(CH$_3$)$_2$ | —CN | H | —C$_6$H$_3$NO$_2$—2-Cl—4 |
| 56 | —CO$_2$CH$_3$ | —CN | H | —C$_6$H$_3$NO$_2$—2-Cl—4 |
| 57 | —CON(piperidine) | —CN | H | —C$_6$H$_3$NO$_2$—2-Cl—4 |
| 58 | —COCH$_2$CH$_3$ | —CN | H | —C$_6$H$_3$NO$_2$—2-Cl—4 |
| 59 | —CON(morpholine) | —CN | H | —C$_6$H$_3$NO$_2$—2-Cl—4 |
| 60 | —CON(piperidine) | —CN | H | —C$_6$H$_3$NO$_2$—2-Cl—4 |
| 61 | —CON(CH$_3$)$_2$ | —CN | H | —C$_6$H$_3$NO$_2$—2-OCH$_3$—4 |
| 62 | —CO$_2$C(CH$_3$)$_3$ | —CN | H | —C$_6$H$_3$NO$_2$—2-Cl—4 |
| 63 | —CON(CH$_3$)$_2$ | —CN | H | —C$_6$H$_3$NO$_2$—2-F—4 |
| 64 | —CON(CH$_3$)$_2$ | —CN | H | —C$_6$H$_3$Cl—2-NO$_2$—4 |
| 65 | —CON(CH$_3$)$_2$ | —CN | H | —C$_6$H$_3$NO$_2$—2-CH$_3$—6 |
| 66 | —CON(CH$_3$)$_2$ | —CN | H | —C$_6$H$_3$NO$_2$—2-Cl—6 |
| 67 | —CON(CH$_3$)$_2$ | —CN | H | —C$_6$H$_4$I—2 |
| 68 | CO—CH(CH$_3$)CH$_2$CH$_3$ | —CN | H | —C$_6$H$_3$NO$_2$—2-Cl—4 |
| 69 | CO—C(CH$_3$)$_3$ | —CN | H | —C$_6$H$_3$NO$_2$—2-Cl—4 |
| 70 | CO—CH$_2$CH(CH$_3$)$_2$ | —CN | H | —C$_6$H$_3$NO$_2$—2-Cl—4 |
| 71 | —CON(CH$_3$)CH$_2$CH$_3$ | —CN | H | —C$_6$H$_3$NO$_2$—2-Cl—4 |

TABLE I-continued

| Example No. | A | B | V | W |
|---|---|---|---|---|
| 72 | —CO$_2$CH$_2$CH$_3$ | —CN | H | —C$_6$H$_3$NO$_2$—2-Cl—4 |
| 73 | —CO$_2$CH(CH$_3$)$_2$ | —CN | H | —C$_6$H$_3$NO$_2$—2-Cl—4 |
| 74 | —CO$_2$CH$_2$CH$_2$CH$_2$CH$_3$ | —CN | H | —C$_6$H$_3$NO$_2$—2-Cl—4 |
| 75 | —COCH$_3$ | —CO$_2$CH$_2$CH$_3$ | Na$^\oplus$ | —C$_6$H$_3$Cl$_2$—2,4 |
| 76 | —COC(CH$_3$)$_3$ | —CN | Mg$^{+2}$ | —C$_6$H$_3$Cl$_2$—2,4 |
| 77 | —COC(CH$_3$)$_3$ | —CN | Mg$^{+2}$ | —C$_6$H$_3$NO$_2$—2-Cl—4 |
| 78 | —COCH(CH$_3$)CH$_2$CH$_3$ | —CN | Mg$^{+2}$ | —C$_6$H$_3$NO$_2$—2-Cl—4 |
| 79 | —CON(CH$_3$)$_2$ | —CN | H | —C$_6$H$_2$Cl$_3$—2,3,5 |
| 80 | —CON(CH$_3$)$_2$ | —CN | H | (furan) |
| 81 | —CON(CH$_3$)$_2$ | —CN | —COC$_6$H$_3$NO$_2$—2-CH$_3$—4 | —C$_6$H$_3$NO$_2$—2-CH$_3$—4 |
| 82 | —CON(CH$_2$CH$_3$)$_2$ | —CN | H | —C$_6$H$_3$NO$_2$—2-Cl—4 |
| 83 | —CON(CH$_3$)$_2$ | —CN | H | —C$_6$H$_3$NO$_2$—2-CH$_3$—4 |
| 84 | —CON(CH$_3$)CH(CH$_3$)$_2$ | —CN | H | —C$_6$H$_3$NO$_2$—2-Cl—4 |
| 85 | —CON(CH$_3$)$_2$ | —CN | H | (3-furyl) |
| 86 | —CON(CH$_3$)$_2$ | —CN | H | (5-nitro-2-furyl) |
| 87 | —CON(CH$_3$)$_2$ | —CN | H | —C$_6$H$_3$NO$_2$—2-Br—4 |
| 88 | —COCH(CH$_3$)$_2$ | —CN | (CH$_3$)$_3$NCH$_2$PMR$^\oplus$ | —C$_6$H$_3$NO$_2$—2-Cl—4 |
| 89 | —COCH(CH$_3$)$_2$ | —CN | H | —C$_6$H$_3$NO$_2$—2-CF$_3$—4 |
| 90 | —CO$_2$C(CH$_3$)$_3$ | —COCH$_3$ | H | —C$_6$H$_3$NO$_2$—2-Cl—4 |
| 91 | —CO$_2$C(CH$_3$)$_3$ | —COCH$_3$ | H | —C$_6$H$_3$Cl$_2$—2,4 |
| 92 | —CON(CH$_3$)$_2$ | —CN | H | (5-chloro-2-thienyl) |
| 93 | —COC(CH$_3$)$_3$ | —CN | K$^\oplus$ | —C$_6$H$_3$NO$_2$—2-Cl—4 |
| 94 | —COC(CH$_3$)$_3$ | —CN | Li$^\oplus$ | —C$_6$H$_3$NO$_2$—2-Cl—4 |
| 95 | —COCH(CH$_3$)$_2$ | —CN | —COC$_6$H$_5$ | —C$_6$H$_3$NO$_2$—2-Cl—4 |
| 96 | —COC(CH$_3$)$_3$ | —CN | —CH$_3$ | —C$_6$H$_3$NO$_2$—2-Cl—4 |
| 97 | —COCH(CH$_3$)$_2$ | —CN | Cu$^{+2}$ | —C$_6$H$_3$NO$_2$—2-Cl—4 |
| 98 | —COC(CH$_3$)$_3$ | —CN | (CH$_3$)$_3$NCH$_2$PMR$^\oplus$ | —C$_6$H$_3$NO$_2$—2-Cl—4 |
| 99 | —COC(CH$_3$)$_3$ | —CN | Cu$^{+2}$ | —C$_6$H$_3$NO$_2$—2-Cl—4 |
| 100 | —COC(CH$_3$)$_3$ | —CN | (CH$_3$)$_2$HNCH$_2$PMR$^\oplus$ | —C$_6$H$_3$NO$_2$—2-Cl—4 |
| 101 | —COC(CH$_3$)$_3$ | —CN | H | —C$_6$H$_4$NO$_2$—2 |
| 102 | —COC(CH$_3$)$_3$ | —CN | H | —C$_6$H$_3$NO$_2$—2-F—5 |
| 103 | —COCH(CH$_3$)$_2$ | —CN | H | —C$_6$H$_4$NO$_2$—2 |
| 104 | —COC(CH$_3$)$_3$ | —CN | H | —C$_6$H$_4$CF$_3$—2 |
| 105 | —COC(CH$_3$)$_3$ | —CN | H | —C$_6$H$_3$NO$_2$—2-Br—4 |
| 106 | —COC(CH$_3$)$_3$ | —CN | H | —C$_6$H$_3$NO$_2$—2-OCH$_3$—4 |
| 107 | —COC(CH$_3$)$_3$ | —CN | H | —C$_6$H$_3$NO$_2$—2-CH$_3$—4 |
| 108 | —COC(CH$_3$)$_3$ | —CN | H | —C$_6$H$_3$NO$_2$—2-CF$_3$—4 |
| 109 | —COC(CH$_3$)$_3$ | —CN | H | —C$_6$H$_3$NO$_2$—2-F—4 |
| 110 | —COC(CH$_3$)$_3$ | —CN | H | —C$_6$H$_3$NO$_2$—2-OCF$_2$H—4 |
| 111 | —COC(CH$_3$)$_3$ | —CN | H | —C$_6$H$_3$NO$_2$—2-CN—4 |
| 112 | —COC(CH$_3$)$_3$ | —CN | H | —C$_6$H$_3$(NO$_2$)$_2$—1,3 |
| 113 | —COC(CH$_3$)$_3$ | —CN | H | —C$_6$H$_3$NO$_2$—2-OCH$_2$CH$_2$CH$_3$—4 |
| 114 | —COC(CH$_3$)(cyclopropyl) | —CN | H | —C$_6$H$_3$NO$_2$—2-Cl—4 |
| 115 | —COC(CH$_3$)$_3$ | —CN | H | —C$_6$H$_3$NO$_2$—2-OCF$_2$CF$_2$H—4 |

EXAMPLE A

Preparation of 4,4-Dimethyl-3-Oxo-Pentanonitrile

To 2.5 l of liquid ammonia containing 2.5 g of anhydrous ferric chloride was cautiously added 132 g of sodium metal portionwise while keeping the temperature of the reaction mixture at −50° C. To this portion was added rapidly a solution of 234 g of acetonitrile diluted with 300 ml of anhydrous diethyl ether followed by the controlled addition of a solution of 332 g methyl pivaloate diluted with 300 ml anhydrous ether at such a rate that the reaction temperature did not exceed −30° C. Allowed reaction to warm up to room temperature overnight. After all of the ammonia has evaporated off, 1 kg of crushed ice is added followed by enough cold water to make the final volume 4.5 l. The mixture is stirred for 30 min., then filtered through a celite bed. The celite was washed well with cold water and 1 l of 1:1 ether/hexane. The phases were separated, discarding the organic layer. The aqueous layer was cautiously acidified with conc. HCl, cooling as necessary to keep the temperature below 35° C. The acidified aqueous phase was extracted with dichloromethane (3×500 ml). The combined organic phases were dried over $MgSO_4$, filtered, and the solvent removed to yield 316 g of the desired product, M.P. 68° C.

EXAMPLE B

Preparation of 2-Nitro-4-Trifluoromethylbenzoic Acid

A slurry of 10 g of 3-nitro-4-cyanobenzotrifluoride in 200 ml of 50% aq $H_2SO_4$ was vigorously refluxed for 2 hours at which time TLC analysis indicated that the reaction was complete. The reaction was poured onto ice, extracted with ether, the ether phase washed with brine, then the ether phase was dried over molecular sieves, filtered and the solvent removed under reduced pressure to yield 9.5 g of a yellow powder, IR (Nujol) 1710 cm$^{-1}$ (C=O).

A solution of 9.8 g of 2-nitro-4-trifluoromethylbenzoic acid and 20 ml thionyl chloride in chloroform/THF was heated to reflux for 7 hours. The volatiles were removed under reduced pressure. The residue was diluted with ether and the solvent removed under reduced pressure to yield 10.2 g of the desired benzoyl chloride, IR (neat) 1795 cm$^{-1}$ (C=O).

EXAMPLE C

Preparation of 2-Nitro-p-Toluic Acid

A slurry of 100 g of 4-chloro-3-nitrotoluene and 80 g of copper (I) cyanide in 500 ml of DMF was refluxed for 12 hours. An additional 20 g of CuCN was added and the reaction refluxed another 4 hours. Ether was added and the ether phase decanted from the dark oil. The ether phase was dried with molecular sieves, filtered and the solvent removed under reduced pressure to yield an orange-brown semi-solid. The semi-solid product was triturated with hexane. The hexane was evaporated off under reduced pressure to yield 30.5 g of the desired product which was used without further purification.

The benzonitrile (10 g) was refluxed for 90 min. in 50% aq $H_2SO_4$. TLC indicated complete hydrolysis of the nitrile. The reaction was pured onto ice and extracted with ether. The ether phase was washed with saturated brine, dried over molecular sieves, filtered and the solvent removed under reduced pressure to yield 4.2 g of the desired product, IR (Nujol) 1695 (C=O—acid), NMR (CDCl$_3$/DMSO/TMS) 2.52 ppm, (S, 3H), 7.80 ppm, (M, 3H). This material was used without further purification in the preparation of the corresponding benzoyl chloride. IR (neat) 1775 cm$^{-1}$ (C=O) acid halide.

EXAMPLE D

Preparation of 2-Nitro-4-Methoxybenzoic Acid

A slurry of 25 g of 2-nitro-4-methoxytoluene and 50 g of $KMnO_4$ in 400 ml of water was refluxed until the purple color was no longer present. The reaction mixture was filtered through a Buchner funnel and the residue washed with 250 ml of boiling water. The filtrate was extracted 3× with ether, acidified then reextracted 3× with THF/CH$_2$Cl$_2$. The combined CH$_2$Cl$_2$ extracts were dried over MgSO$_4$, filtered, and the solvent removed under reduced pressure to yield 4.5 g of the product as a white solid, mp 193°-5° C.

EXAMPLE 25

Preparation of N,N-Dimethyl-Alpha-Ethoxy Carbonyl-Beta-Methoxy-2,4-Dichloro Cinnamamide A mixture of 5.0 g (0.015 mole) of N,N-dimethylalpha-ethoxycarbonyl-beta-hydroxy-2,4-dichlorocinnamamide and 4.14 g (0.03 mole) anhydrous powdered K$_2$CO$_3$ in 100 ml MEK was heated to reflux for 30 minutes then cooled to room temperature. To the slurry was added 2.44 g (0.0165 mole) CH$_3$I dropwise. The reaction mixture was stirred at room temperature an additional 30 minutes then heated to reflux for 2 hours and then cooled again to room temperature. The reaction was worked-up by diluting with 200 ml ether washing successively with water (2×100 ml) and 10% NaHCO$_3$ (2×100 ml) and then drying the organic phase over anhydrous MgSO$_4$, filtering, and stripping off the ether to yield 5.2 g of a semi-solid. The semi-solid was crystallized from ether/hexanes to yield 4.0 g of the product, mp 88°-92°.

EXAMPLE 26

Preparation of N,N-Dimethyl-Beta-BenzyloxyAlphaethoxycarbonyl-2,4-Dichlorocinnamamide A well stirred slurry of 10.0 g of N,N-dimethylalpha-ethoxycarbonyl-beta-hydroxy-2,4-dichlorocinnamamide, 8.3 g of powdered anh. K$_2$CO$_3$, and 100 ml of dry DMSO was heated to 100° C. for 30 min. To this mixture was added 6.5 g of benzyl iodide all at once and the mixture heated at 120° C. for 1 hour. The reaction was cooled to RT, 100 ml of CH$_2$Cl$_2$ and 100 ml of water added plus a few drops of concentrated HCl. The organic phase was collected, washed with saturated brine, dried with MgSO$_4$, filtered and concentrated under reduced pressure to yield a light yellow gum. The crude product was taken up in a minimum amount of ether/hexane and the product allowed to crystallize, yielding 4.0 g of white solid, MP 115° C.

EXAMPLE 28

Preparation of N,N-Dimethyl-Beta-BenzoyloxyAlphaethoxycarbonyl-2,4-Dichlorocinnamamide To a well stirred mixture of 12.4 g of N,N-dimethylalphaethoxycarbonyl-beta-hydroxy-2,4-dichlorocinnamamide, 4.0 g of triethylamine and 150 ml of dry ether at 4° C. was added dropwise benzoyl chloride at such a rate that the temperature did not exceed 5° C. The reaction was allowed to warm up to room temperature, stirred at this temperature for 2 hours, the cooled again to 4° C. The solids were filtered off and the filtrate concentrated under reduced pressure to yield 12.0 g of a white solid. The solid was crystallized from ether/hexane to yield 8.0 g of the desired product, m.p. 106° C.

EXAMPLE 39

Preparation of N,N-Dimethyl-2-(2-Nitro-4-Chlorobenzoyl)-2-Cyanoacetamide

Method 1

To a cooled (10°–15° C.) solution of 14.4 g (0.128 mole) of N,N-dimethyl cyanoacetamide, 40 ml (0.287 mole) triethylanine, and 100 mg 4-dimethylaminopyridine in 100 ml tetrahydrofuran (THF) under $N_2$ was slowly added 56.6 g (0.257 mole) of 2-nitro-4-chlorobenzoyl chloride portionwise and the reaction allowed to warm to room temperature and stir overnight.

The solvents were stripped off, and the residue slurried in $CH_2Cl_2$. The organic phase was extracted with 2M NaOH (3×), the combined aqueous phase filtered and acidified to pH 2 with conc. HCl (with cooling) and extracted with $CH_2Cl_2$ (4×). The combined organic extracts were dried over anhydrous $MgSO_4$, filtered, and the solvents removed in vacuo to yield the crude product as a dark brown semi-solid. The crude product was slurried in a minimal amount of $Et_2O$ and filtered to yield 29 g of impure product. Recrystallization from EtOAc yielded 18.8 g (49.7%) of yellow crystals, mp 114.5–116.5.

Method 2

To a cooled (10°–15° C.) solution of 14.4 g (0.128 mole) of N,N-dimethyl cyanoacetamide, 40 ml (0.287 mole) triethylanine, and 100 mg 4-dimethylaminopyridine in 100 ml tetrahydrofuran (THF) under $N_2$ was slowly added 56.6 g (0.25 mole) of 2-nitro-4-chlorobenzoyl chloride portionwise and the reaction allowed to warm to room temperature and stir overnight.

The solvents were stripped off and the residue slurried in ether. The organic phase was dried over $MgSO_4$ passed through a silica gel column and the solvents stripped off to yield a crude yellow solid. Trituration of the crude solid with EtOAc yielded 34% of N,N-dimethylalpha-cyano-beta-(2-nitro-4-chlorobenzoyloxy)-2-nitro-4-chlorocinnamamide as an off white solid, mp 137°–146° C., as a mixture of double bond isomers.

To a stirred room temperature solution of 0.7 g (0.013 mole) of $NaOCH_3$ in methanol under $N_2$ was added 4.0 g (0.0086 mole) of the above cinnamamide portionwise with slight cooling and the reaction allowed to stir at room temperature overnight. Within 2 hours, the reaction mixture had become homogeneous. The reaction was worked up by stripping off the solvent, adding water and 2M NaOH, and extracting the aqueous phase with ether (3×). The organic extracts contained methyl benzoate and were discarded. The aqueous phase was acidified with conc. HCl to approximately pH 2, and $MgSO_4$, filtered and stripped off to yield 2.1 g of a crude yellow solid. Trituration of the solid with ether yielded 1.2 g (47%) of the desired product, mp 113°–114.5° C.

EXAMPLE 44

Preparation of N,N-Dimethyl-Alpha-Cyano-BetaHydroxy-2-Nitro-4-Trifluoromethylcinnamamide To a well stirred solution of 5.0 g of N,N-dimethylcyanoacetamide, 8 ml of triethylamine, and 0.05 g of p-dimethylaminopyridine dissolved in 8 ml of dry THF was added 10 g of 2-nitro-4-trifluoromethylbenzoyl chloride dissolved in a min. amount of THF at such a rate that the reaction temperature did not exceed 45° C. The reaction was stirred overnight, at which time TLC analysis indicated that the reaction was complete. The reaction was worked up by removing the solvents under reduced pressure, diluting the residue with 15% NaOH, and extracting well with ether. The aqueous phase was acidified and extracted with 2×100 ml of $CH_2Cl_2$. The combined $CH_2Cl_2$ extracts were washed once with saturated brine, dried over molecular sieves, filtered, and then passed through a short column of silica gel. The eluate was concentrated under reduced pressure to yield 9.8 g of an orange oil that solidified upon standing. The impure solid was crystallized from ether/hexane to yield 4.24 g of the product, m.p. 104°–6° C.

EXAMPLE 55

Preparation of Bromine Addition Product of 1-(2-Nitro-4-Chlorophenyl)-2-Cyano-4-Methyl-1,3-Dioxo-1-Pentane To a stirred room temperature solution of 3 g of 1-(2-nitro-4-chlorophenyl)-2-cyano-3-oxo-4-methyl-1-pentene dissolved in 25 ml $CCl_4$ is added 3.0 g $Na_2CO_3$ and 1 ml $Br_2$. The slurry is stirred at RT for 1½ hours. The $CCl_4$ was washed 3× with water then dried over $Na_2SO_4$, filtered and evaporated to dryness to yield 4.0 g of 1-(2-nitro-4-chlorophenyl)-2-bromo-2-cyano-4-methyl-1,3-dioxo-1-pentane as a yellow oil.

EXAMPLE 69

Preparation of 1-(2-Nitro-4-Chlorophenyl-1-Hydroxy-2-Cyano-3-Oxo-4,4-Dimethyl-1-Pentene Method 1

In a 2.0 liter, 4 necked RBF with mechanical stirrer, heating mantle and condenser, 22.0 g of turnings magnesium (0.90 mole), 300 ml of absolute ethanol and 50 ml of carbontetrachloride are combined and the resulting exotherm causes a vigorous reflux. When the pot temperature starts to drop, a clear solution of 300 ml absolute ethanol and 75.0 g of cyano-trimethyl acetone (4,4-dimethyl-3-oxo-pentanonitrile) (0.60 mole) is added dropwise maintaining a mild reflux. The reaction is then heated for 4.0 hours at reflux or until all magnesium is completely reacted.

Vacuum distillation is used to remove solvent. The residual white solid is absolutely freed of ethanol by taking this solid into 500 ml of toluene and concentrating again.

The reaction flask is removed from the rotary evaporator and the solids dissolved in 900 ml of hot toluene. To this solution is added at once 145.0 g of 4-chloro-2-nitrobenzoyl chloride (0.66 mole) in 100 ml of toluene. The reaction temperature is brought up to 100° C. and then let slowly cool and the stirring is continued for another 2.0 hours.

The reaction is worked up by adding 350 ml H₂O, followed by 250 ml concentrated HCl with stirring. The aqueous phase is separated and extracted by 200 ml of ether before discarding. The combined organics are dried and concentrated then redissolved in 600 ml ether. The ether solution is first washed by 500 ml H₂O and then extracted twice, each by 500 ml of 5% NaHCO₃ solution followed by a 500 ml H₂O. The aqueous extractions are combined and slowly acidified by 1600 ml of 2N HCl solution.

The acidified aqueous solution is extracted 2×300 ml CH₂Cl₂ and the combinedorganics are dried with MgSO₄, filtered and rotovaped. The collected red oily concentrate is solidified in 500 ml of hexane and the resulting solid is filtered, washed thoroughly by hexane and dried.

A 135.0 g of light yellow solid product is received and its m.p. is recorded at 69°–71° C.

Method 2

In a 2.0 liter 4-necked RBF with mechanical stirrer, heating mantle, and condenser 75.0 g of cyano-trimethyl acetone (0.60 mole) is dissolved in 750 ml of dry toluene. To this is added 10.5 g of LiH (1.30 mole) portionwise with stirring at room temperature. Let stir at room temperature for 3 hours or until no additional hydrogen evolves. Stir at 40° overnight.

The next morning bring the temperature up to 60° and add 145 g of 4-chloro-2-nitrobenzoyl chloride (0.66 mole). Increase the stirring speed during the addition. After the addition is complete, heat the mixture as rapidly as possible to 100° with forceful stirring. Upon reaching 100, turn off the heating mantle and let temperature fall slowly back to room temperature (2 hours).

The reaction mixture is then vacuum filtered. The yellow solid is slurried in 400 ml of toluene and filtered again. The solid is now suspended in 800 ml of ether. With stirring, 350 ml of water followed by 250 ml concentrated HCl is added to the ether solution. The aqueous phase is separated and extracted with an additional 200 ml of ether before discarding. The ether solution is then washed by 500 ml of water followed by three alternating extractions with 500 ml each NaHCO₃ solution and water. All the aqueous extractions are combined and slowly acidified with concentrated HCl.

The acidified aqueous solution is extracted twice with 300 ml of methylene chloride and the combined organics are dried over MgSO₄, filtered and rotovaped. The collected red oil is solidified in 500 ml cold hexane. The solid is filtered and washed with cold hexane and dried.

A pale yellow solid product is obtained 108 g (60% yield). Melting point 77.5°–78.5°.

EXAMPLE 71

Preparation of
2-(4-Chloro-2-Nitrobenzoyl)-2-Cyano-N-Ethyl-N-MethylAcetamide 2-cyano-N-ethyl-N-methylacetamide (5.56 g; 0.044 mol) and triethylamine (13.36 g; 0.132 mol) were dissolved in dry THF (100 ml) under dry nitrogen, and 4-chloro-2-nitrobenzoyl chloride (9.68 g; 0.044 mol) in dry THF (100 ml) added dropwise over 45 min. The mixture was stirred at room temperature under dry nitrogen for 18 hours, during which time a precipitate was formed. The solution was filtered, washing the solid with THF and adding the washings to the solution, and evaporated, giving a residue which was treated with 2M sodium hydroxide solution (200 ml), and this then washed with CH₂Cl₂ (2×100 ml). The aqueous solution was acidified to pH 1 with concentrated hydrochloric acid, and extracted into CH₂Cl₂ (3×200 m). The extracts were combined, dried (Na₂SO₄), filtered and evaporated, giving a very viscous oil which solidified. Trituration with ether (20 ml) gave 2-(4-chloro-2-nitrobenzoyl)-2-cyano-N-ethyl-N-methylacetamide (6.10 g; 45%) as a solid, m.p. 95°–98° C., (Found, C: 49.60; H: 3.87; N: 13.25; Cl: 12.28. C₁₃H₁₂ClN₃O₄ requires C: 50.40; H: 3.88; N: 13.57; Cl: 11.47%, d (CDCl₃); 60 MHz) 1.3 (3H, t, J=7, Hz), 3.2 (3H, s), 3.7 (2H, q, J=7 Hz), 7.4–7.55 (1H, d, J=8 Hz), 7.6–7.8 (1H, dd, J=8, 2 Hz), 8.1 (1H, d, J=2 Hz) and 16.4 (1H, br, s), νmax (nujol) 2200, 1590 (shoulder) and 1500.

EXAMPLE 74

Preparation of Butyl
2-(4-Chloro-2-nitrobenzyl)-2-Cyanoacetate

Butyl cyanoacetate (6.35 g; 0.05 mol) and triethylamine (20.9 ml; 0.15 mol) were dissolved in dry THF (100 ml) under dry nitrogen, and 4-chloro-2-nitrobenzoyl chloride (11.0 g; 0.05 mol) in dry THF (100 ml) added dropwise over 45 min. The mixture was stirred at room temperature under dry nitrogen for 18 hours, during which time a precipitate was formed. The solution was filtered and evaporated, giving a residue which was treated with 2M sodium hydroxide solution (200 ml) and CH₂Cl₂ (100 ml). This formed three layers. The middle layer was treated with 2M hydrochloric acid (50 ml) and extracted into CH₂Cl₂ (3×50 ml). The extracts were combined, dried (Na₂SO₄), filtered and evaporated, giving butyl 2-(4-chloro-2-nitrobenzoyl)-2-cyanoacetate (10.27 g; 63%) as a yellow solid, m.p. 56°–58° C., (Found, C: 52.01; H: 4.05; N: 8.70; Cl: 10.97. C₁₄H₁₃ClN₂O₅ requires C: 51.77; H: 4.01; N: 8.63; Cl: 10.94%), d (CDCl₃; 60 MHz) 0.8–2.1 (7H, m), 4.4 (2H, t, J=6 Hz), 7.65 (2H, m), 8.15 (1H, d, J=2 Hz) and 13.0 (1H, br, s), νmax (nujol) 2230, 1660, 1610, 1590 and 1540.

EXAMPLE 77

Preparation of
bis-(2-Cyano-4,4-Dimethyl-1-Oxido-3-Oxo-(2-Nitro-4-Chlorophenyl)-1-Pentene) Magnesium Salt Use preparation of 2-cyano-4,4-dimethyl-1-hydroxy-3-oxo-1-(2-nitro-4-chlorophenyl)-1-pentene.

The reaction mixture was worked-up by filtering off the crude solid product and washing the solid with toluene. The crude salts were placed in an erlenmeyer flask, ether and water added, and the organic phase separated and dried over MgSO₄. The ether was removed under reduced pressure to yield the product as a yellow solid.

EXAMPLE 89

Preparation of
2-Cyano-1-Hydroxy-4-Methyl-3-Oxo-1-(2-Nitro-4-Trifluoromethylphenyl)-1-Pentene To a well stirred suspension of 3.1 g of washed NaH in 50 ml of dry toluene at room temperature was slowly added a solution of 3.9 g of isopropyl cyanomethylketone in 25 ml of toluene. After stirring an additional 5 min. at ambient temperature, a solution of 11.7 g of 2-nitro-4-trifluoromethylbenzoyl chloride in 25 ml of dry toluene was added at such a rate that the temperature of the reaction did not exceed 50° C. The reaction was heated at 50° C. for 2 hours then allowed to stir at RT overnight.

The reaction mixture was cautiously poured into 300 ml of water and the resulting mixture extracted with ether (2×250 ml) and the organic phase discarded. The aqueous phase was acidified and extracted with $CH_2Cl_2$/ether (2×200 ml). The combined organic phase was passed through a short column of silica gel and the solvents removed under reduced pressure. The resulting oil was diluted with $CH_2Cl_2$ and chromatographed over silica gel. The material eluting with 100% $CH_2Cl_2$ (3.1 g of a brown solid) was triturated with hot hexane. The desired product crystallized out of the hexane as a tan solid, yield 1.4 g, m.p. 83°–5° C.

EXAMPLE 94

Preparation of
2-Cyano-4,4-Dimethyl-1-Oxido-3-Oxo-1-(2-Nitro-4-Chlorophenyl)-1-Pentene Lithium Salt To a stirred slurry of 0.36 g of LiH in 15 ml of dry ether under $N_2$ at room temperature was rapidly added a solution of 1.5 g of 2-cyano-4,4-dimethyl-1-hydroxy-3-oxo-1-(2-nitro-4-chlorophenyl)-1-pentene dissolved in 15 ml of dry ether. The reaction mixture turned brown and a precipitate formed with 5 min. Enough dry THF was added to dissolve the solid and the mixture allowed to stir overnight at ambient temperature. The reaction was filtered and the filtrate concentrated under reduced pressure to yield 1.25 g of product as a yellow solid, m.p. >230° C. (decomp.).

EXAMPLE 96

Preparation of
2-Cyano-4,4-Dimethyl-1-Methoxy-3-Oxo-(2-Nitro-4-Chlorophenyl)-1-Pentene To a solution of 1.0 g of 2-cyano-4,4-dimethyl-1-hydroxy-3-oxo-(2-nitro-4-chlorophenyl)-1-pentene dissolved in 3 ml of dry THF was cautiously added an ethereal solution of diazomethane. The excess starting material was removed by washing the reaction mixture with cold 3% $K_2CO_3$, separating the phases, drying the organic phase over $MgSO_4$, filtering, and concentrating under reduced pressure. The crude product was crystalized from hot hexane/THF to yield 250 mg of the product, m.p. 130°–1° C.

EXAMPLE 98

Preparation of
2-Cyano-4,4-Dimethyl-1-Hydroxy-3-Oxo-(2-Nitro-4-Chlorophenyl)-1-Pentene Complexed to a Strong Base (Hydroxide Form) Ultrafine Polystyrene Macroreticular Resin To a solution of 2.0 g of 2-cyano-4,4-dimethyl-1-hydroxy-3-oxo-1-(2-nitro-4-chlorophenyl)-1-pentene in ether was added 1.0 g of a strong base (hydroxide form) ultrafine polystyrene macroreticular resin ground to an average particle size of about one (1) micron (16.3% in water). The mixture was centrifuged and the ether decanted off. The ether was stripped off to yield 800 mg of material that had not been loaded onto the resin. The resin was suspended in methanol and used as is for biological evaluations.

EXAMPLE 99

Preparation of the
bis-(2-Cyano-4,4-Dimethyl-1-Oxido-3-Oxo-1-(2-Nitro-4-Chlorophenyl)-1-Pentene) Copper (II) Salt To a concentrated solution of 2.0 g of 2-cyano-4,4-dimethyl-1-hydroxy-3-oxo-1-(2-nitro-4-chlorophenyl)-1-pentene in a min. amount of methanol was added a hot solution of 10 ml of 0.55M Cu(Ac)2. A precipitate formed immediately. The solid was collected and crystallized from 2-propanol, m.p. 248°–9° dec.

EXAMPLE 100

Preparation of
2-Cyano-4,4-Dimethyl-1-Hydroxy-3-Oxo-(2-Nitro-4-Chlorophenyl)-1-Pentene Complexed to a Weak Base (Free Base Form) Polystyrene Ultrafine Macroreticular Resin Substantially following the procedures for Example 98, 1.2 g of 2-cyano-4,4-dimethyl-1-hydroxy-3-oxo-(2-nitro-4-chlorophenyl)-1-pentene was complexed onto 1.0 g of a weak base (free base form) polystyrene ultrafine macroreticular resin ground to an average particle size of about one (1) micron.

EXAMPLE 101

Preparation of
2-Cyano-4,4-Dimethyl-1-Hydroxy-3-Oxo-1-(2-Nitrophenyl)-1-Pentene

The magnesium salt of 3-oxo-4,4-dimethylpentanonitrile was prepared as previously described. To this salt was added 60 ml of dry toluene and the mixture warmed to 60° C. A solution of 2-nitrobenzoyl chloride dissolved in 60 ml of dry toluene was rapidly added to the slurry. Heating was continued until the mixture began to reflux, then the reaction mixture was allowed to slowly cool to room temprature and stirring was continued overnight. To the RT mixture was added 200 ml of 6N HCl and stirring continued until all of the solids had dissolved. The phases were separated, the aqueous phase extracted with ether (2×100 ml), and the organic phases combined. The combined organic phases were extracted with 75 ml of ½ saturated $NaHCO_3$ and then 75 ml of water. This was repeated two more times, all of the aqueous phases combined and acidified to a Congo Red end point with concentrated HCl, and the acidified aqueous phase extracted with ether (3×100 ml). The combined ether extracts were washed with brine, dried with $MgSO_4$, filtered, and concentrated under reduced pressure. The residue was triturated with hot water and dried to yield 2.5 g of a light tan solid, m.p. 111°–2° C.

EXAMPLE 104

Preparation of
1-(2-Trifuoromethylphenyl)-1-Hydroxy-2-Cyano-3-Oxo-4,4-Dimethyl-1-Pentene Prepared according to the procedure for Example 69, Method 2 with the substitution of 2-trifluoromethylbenzoyl chloride for 2-nitro-4-chlorobenzoyl chloride. M.P. 101°–106° C.

EXAMPLE 106

Preparation of
1-(2-Nitro-4-Methoxyphenyl)-1-Hydroxy-2-Cyano-3-Oxo-4,4-Dimethyl-1-Pentene Prepared according to the procedure for Example 69, Method 1, with the substitution of 2-nitro-4-methoxybenzyl chloride for 2-nitro-4-chlorobenzoyl chloride. M.P. 85°–88° C.

EXAMPLE 107

Preparation of
1-(2-Nitro-4-Methylphenyl)-1-Hydroxy-2-Cyano-3-Oxo-4,4-Dimethyl-1-Pentene Prepared according to the procedure for Example 69, Method 1 with 2-nitro-4-methylbenzyl chloride substituting for 2-nitro-4-chlorobenzoyl chloride. M.P. 99°–102° C.

EXAMPLE 108

Preparation of
2-Cyano-4,4-Dimethyl-1-Hydroxy-3-Oxo-1-(2-Nitro-4-Trifluoromethylphenyl)-1-Pentene Method 1

To a solution of 20 ml of ethanol and 10 drops of CCl$_4$ was added 0.67 g of magnesium turnings. Heat was applied until the reaction began. To this mixture was added a solution of 3.13 g of 3-oxo-4,4-dimethylpentanonitrile dissolved in a minimum amount of methanol and the mixture gently heated until all of the magnesium turnings reacted. The ethanol was removed under reduced pressure, toluene was added and removed under reduced pressure to insure all of the ethanol had been removed. The off-white magnesium salt was slurried in 40 ml of dry toluene, the mixture heated to 50° C. and to the heated slurry was added a solution of 7.61 g of 2-nitro-4-trifluoromethylbenzoyl chloride dissolved in 20 ml of toluene all at once. The reaction mixture was heated to reflux for 1 hour then allowed to stir overnight at room temperature. The gummy yellow slurry waas treated with 200 ml of 6N HCl and stirred until all of the solids had dissolved. The phases were separated, the aqueous phase washed with ether (2×75 ml) and all of the organic phases combined. The combined organic phases were washed with ½ saturated NaHCO$_3$ (2×100 ml), the combined bicarbonate extracts carefully neutralized with concentrated HCl, and the acidic aqueous phase extracted with ether (3×75 ml). The combined ether extracts were washed with saturated brine, dried with MgSO$_4$, filtered, and concentrated under reduced pressure. The residue was crystallized from hot hexane to yield 2.8 g of a tan solid, m.p. 53°–56° C.

Method 2

Prepared according to the procedure for Example 70, Method 2 with 2-nitro-4-trifluoromethylbenzoyl chloride substituted for 2-nitro-4-chlorobenzoyl chloride. m.p. 53°–56° C.

Following the procedures of the illustrative examples described above and conventional procedures known to those skilled in the art, other enols of Formula I are prepared.

The novel compounds of the present inventions are useful both as preemergence and as postemergence herbicides and are particularly useful as preemergence herbicides. Preemergence herbicides are ordinarily used to treat the soil in which the desired crop is to be planted by application either before seeding, during seeding, or after seeding and before the crop emerges. Preemergence herbicides may be applied to the soil surface or incorporated into the soil up to a depth of about four inches into which crop seed will be planted. Postemergence herbicides are those which are applied after the plants have emerged and during their growth period.

The novel compounds of the present invention may be advantageously employed as weed killers in crops of both monocots and dicots and are particularly active against nutsedge (Cyperus spp.) while demonstrating substantial safety to important agronomic crops such as soybeans, corn and cotton.

The present enols may be applied in any amount which will give the required control of weeds. A preferred rate of application of the herbicides of the invention is from about 0.01 to about 12 and especially preferred from about 0.01 to about 5 pounds of the enol compounds per acre.

Under typical conditions, the enols of the present invention may be applied to the soil surface prior to crop emergence or advantageously incorporated into the soil or other growth medium prior to planting a crop. This incorporation can be carried out by any convenient means, including by simply mixing with the soil, by applying the enol to the surface of the soil and then disking or dragging into the soil to the desired depth, or by employing a liquid carrier to accomplish the necessary penetration and impregnation.

An enol of the present invention can be applied to the growth medium or to plants to be treated either by itself, or, as is generally done, as a component in a herbicidal composition or formulation which also comprises an agronomically acceptable carrier. By agronomically acceptable carrier is meant any substance which can be used to dissolve, disperse or diffuse a herbicidal compound in the composition without impairing the effectiveness of the herbicidal compound and which by itself has no detrimental effect on the soil, equipment, crops, or agronomic environment. Mixtures of the enols of the present invention may also be used in any of these herbicidal formulations. The herbicidal compositions of the invention can be either solid or liquid formulations or solutions. For example, the enols can be formulated as wettable powders, emulsifiable concentrates, dusts, granular formulations, aerosols or flowable emulsion concentrates. In such formulations, the compounds are extended with a liquid or solid carrier and, when desired, suitable surfactants are incorporated.

It is usually desirable, particularly in postemergence applications, to include adjuvants such as wetting agents, spreading agents, dispersing agents, sticking agents, adhesives and the like, in accordance with agricultural practices. Examples of adjuvants which are commonly used in the art can be found in the John W. McCutcheon, Inc. publication "Detergents and Emulsifiers Annual."

The enol compounds of this invention can be dissolved in any appropriate solvent. Examples of solvents which are useful in the practice of this invention include alcohols, ketones, aromatic hydrocarbons, halogenated hydrocarbons, dimethylformamide, dioxane, dimethyl sulfoxide, and the like. Mixtures of these solvents can also be used. The concentration of enol in the solution can vary from about 2% to about 98% with a preferred range being from about 25% to about 75%.

For the preparation of emulsifiable concentrates, the enols can be dissolved in organic solvents such as toluene, xylene, methylated naphthalene, corn oil, pine oil, o-dichlorobenzene, isophorone, cyclohexanone, methyl oleate, and the like, or in mixtures of these solvents, together with an emulsifying agent which permits dispersion in water. Suitable emulsifiers include, for example, the ethylene oxide derivatives of alkylphenols or long-chain alcohols, mercaptans, carboxylic acids, and reactive amines and partially esterified polyhydric alcohols, and the like. Solvent-soluble sulfates or sulfonates, such as the alkaline earth salts or amine salts of alkylbenzenesulfonates and the fatty alcohol sodium sulfates, having surface-active properties can be used as emulsifiers either alone or in conjunction with an ethylene oxide reaction product. Flowable emulsion concentrates are formulated similarly to the emulsifiable concentrates and include, in addition to the above components, water and a stabilizing agent such as a water-soluble cellulose derivative or a water-soluble salt of a polyacrylic acid. The concentration of the active ingredient in emulsifiable concentrates is usually from about 10% to about 60% and in flowable emulsion concentrates, this can be as high as about 75%.

Wettable powders suitable for spraying can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of from about 20% to about 98% preferably from about 40% to about 75%. A dispersing agent can constitute from about 0.5% to about 3% of the composition, and a wetting agent can constitute from about 0.1% to about 5% of the composition.

Dusts can be prepared by mixing the compounds of the invention with finely divided inert solids which may be organic or inorganic in nature. Materials useful for this purpose include, for example, botanical flours, silicas, silicates, carbonates and clays. One convenient method of preparing a dust is to dilute a wettable powder with a finely divided carrier. Dust concentrates containing from about 20% to about 80% of active ingredient are commonly made and subsequently diluted to from about 1% to about 10% use concentration.

Granular formulations can be prepared by impregnating a solid such as granular fuller's earth, vermiculite, ground corn cobs, seed hulls, including bran or other grain-hulls, or similar material. A solution of one or more of the enols of the present invention in a volatile organic solvent can be sprayed or mixed with the granular solid and the solvent then removed by evaporation. The granular material may be of any suitable size, with a preferred size range of from about 16 to about 60 mesh. The enol will usually comprise from about 2% to about 15% of the granular formulation.

The enols of the present invention can also be mixed with fertilizers or fertilizing materials before their application. In one type of solid fertilizing composition in which the enols may be used, particles of a fertilizer or fertilizing ingredients, such as ammonium sulfate, ammonium nitrate, or ammonium phosphate can be coated with one or more of the enols. The solid enol and solid fertilizing material may also be admixed in blending or mixing equipment, or they can be incorporated with fertilizers in granular formulations. Any relative proportion of enol and fertilizer can be used which is suitable for the crops and weeds to be treated. The enols will commonly be from about 5% to about 25% of the fertilizing composition. These compositions provide fertilizing materials which promote the rapid growth of desired plants, while at the same time control the growth of undesired plants.

The enols of the present invention may be applied as herbicidal sprays by methods commonly employed, such as conventional high-gallonage hydraulic sprays, low gallonage sprays, airblast spray, aerial sprays, and dusts. If low volume applications are desired, a solution of the compound is usually used. The dilution and rate of application will usually depend upon such factors as the type of equipment employed, method of application, area to be treated and the type and stage of development of the weeds.

For some applications, it may be desired to add one or more other herbicides along with enols of the present invention, thereby providing additional advantages and effectiveness. When mixtures of herbicides are employed, the relative proportions which are used will depend upon the crop to be treated and the degree of selectivity in weed control desired. Examples of other herbicides which can be incorporated with the enols of the present invention include:

Carboxylic Acids and Derivatives 2,3,6-trichlorobenzoic acid and its salts;
2,3,5,6-tetrachlorobenzoic acid and its salts;
2-methoxy-3,5,6-trichlorobenzoic acid and its salts;
2-methoxy-3,6-dichlorobenzoic acid and its salts;
2-methyl-3,6-dichlorobenzoic acid and its salts;
2,3-dichloro-6-methylbenzoic acid and its salts;
2,4-dichlorophenoxyacetic acid and its salts and esters;
2,4,5-trichlorophenoxyacetic acid and its salts and esters;
2-methyl-4-chlorophenoxyacetic acid and its salts and esters;
2-(2,4,5-trichlorophenoxy)propionic acid and its salts and esters;
4-(2,4-dichlorophenoxybutyric acid and its salts and esters;
4-(2-methyl-4-chlorophenoxy)butyric acid and its salts and esters;
2,3,6-trichlorophenylacetic acid and its salts;
3,6-endoxohexahydrophthalic acid;
dimethyl 2,3,5,6-tetrachloroterephthalate;
trichloroacetic acid and its salts;
2,2-dichloropropionic acid and its salts;
2,3-dichloroisobutyric acid and its salts;

Carbamic Acid Derivatives ethyl N,N-di(n-propyl)thiolcarbamate;
propyl N,N-di(n-propyl)thiolcarbamate;
ethyl N-ethyl-N-(n-butyl)thiolcarbamate;
propyl N-ethyl-N-(n-butyl)thiolcarbamate;
2-chloroallyl N,N-diethyldithiocarbamate;
N-methyldithiocarbamic acid salts;
ethyl 1-hexamethyleneiminecarbothiolate;
isopropyl N-phenylcarbamate;
isopropyl N-(m-chlorophenyl)carbamate;
4-chloro-2-butynyl N-(m-chlorophenyl)carbamate;
methyl N-(3,4-dichlorophenyl)carbamate;

Phenols dinitro-o-(sec-butyl)phenol and its salts;
pentachlorophenol and its salts;

Substituted Ureas 3-(3,4-dichlorophenyl)-1,1-dimethylurea;
3-phenyl-1,1-dimethylurea;
3-(3,4-dichlorophenyl)-3-methoxy-1,1-dimethylurea;
3-(4-chlorophenyl)-3-methoxy-1,1-dimethylurea;
3-(3,4-dichlorophenyl)-1-n-butyl-1-methylurea;
3-(3,4-dichlorophenyl)-1-methoxy-1-methylurea;
3-(4-chlorophenyl)-1-methoxy-1-methylurea;
3-(3,4-dichlorophenyl)-1,1,3-trimethylurea;
3-(3,4-dichlorophenyl)-1,1-diethylurea; dichloral urea;

Substituted Triazines 2-chloro-4,6-bis(ethylamino)-s-triazine;
2-chloro-4-ethylamino-6-isopropylamino-s-triazine;
2-chloro-4,6-bis(methoxypropylamino)-s-triazine;
2-methoxy-4,6-bis(isopropylamino)-s-triazine;
2-chloro-4-ethylamino-6-(3-methoxypropylamino)-s-triazine;
2-methylmercapto-4,6-bis(isopropylamino)-s-triazine;
2-methylmercapto-4,6-bis(ethylamino)-s-triazine;
2-methylmercapto-4-ethylamino-6-isopropylamino-s-triazine;
2-chloro-4,6-bis(isopropylamino)-s-triazine;
2-methoxy-4,6-bis(ethylamino)-s-triazine;
2-methoxy-4-ethylamino-6-isopropylamino-s-triazine;
2-methylmercapto-4-(2-methoxyethylamino)-6-isopropylaimo-s-triazine;
4-amino-6-t-butyl-3-(methylthio)-as-triazine-5(4H)-one;

Diphenyl Ether Derivatives 2,4-dichloro-4'-nitrodiphenyl ether;
2,4,6-trichloro-4'-nitrodiphenyl ether;
2,4-dichloro-6-fluoro-4'-nitrodiphenyl ether;
3-methyl-4'-nitrodiphenyl ether;
3,5-dimethyl-4'-nitrodiphenyl ether;
2,4'-dinitro-4-trifluoromethyldiphenyl ether;
2,4-dichloro-3'-methoxy-4'-nitrodiphenyl ether;

Anilides

N-3,4-dichlorophenyl)propionamide;
N-(3,4-dichlorophenyl)methacrylamide;
N-(3-chloro-4-methylphenyl)-2-methylpentanamide;
N-(3,4-dichlorophenyl)trimethylacetamide;
N-(3,4-dichlorophenyl)-alpha,alpha-dimethylvaleramide;
N-isopropyl-N-phenylchloroacetamide;
N-n-butoxymethyl-N-(2,6-diethylphenyl)chloroacetamide;
N-n-methoxymethyl-N-(2,6-diethylphenyl)chloroacetamide;

Uracils 5-bromo-3-s-butyl-6-methyluracil;
5-bromo-3-cyclohexyl-1,6-dimethyluracil;
3-cyclohexyl-5,6-trimethyleneuracil;
5-bromo-3-isopropyl-6-methyluracil;
3-tert-butyl-5-chloro-6-methyluracil;

Nitriles 2,6-dichlorobenzonitrile;
diphenylacetonitrile;
3,5-dibromo-4-hydroxybenzonitrile;
3,5-diiodo-4-hydroxybenzonitrile;

Other Organic Herbicides 2-chloro-N,N-diallylacetamide'
N-(1,1-dimethyl-2-propynyl)-3,5-dichlorobenzamide;
maleic hydrazide;
3-amino-1,2,4-triazole;
monosodium methanearsonate;
disodium methanearsonate;
N,N-dimethyl-alpha,alpha-diphenylacetamide;
N,N-di(n-propyl)-2,6-dinitro-4-trifluoromethylaniline;
N,N-di(n-propyl)-2,6-dinitro-4-methylaniline;
N,N-di(n-propyl)-2,6-dinitro-4-methylsulfonylaniline;
O-(2,4-dichlorophenyl)-O-methyl-isopropylphosphoramidothioate;
4-amino-3,5,6-trichloropicolinic acid;
2,3-dichloro-1,4-naphthoquinone;
di(methoxythiocarbonyl)disulfide;
3-isopropyl-1H-2,1,3-benzothiadiazin-(4)3H-one-2,2-dioxide;
6,7-dihydrodipyridol[1,2-a:2',1'-c]pyrazidinium salts;
1,1'-dimethyl-4,4'-bipyridinium salts;
3,4,5,6-tetrahydro-3,5-dimethyl-2-thio-2H-1,3,5-thiadiazine.

The herbicidal activity of enols of the present invention towards a number of common weeds was evaluated using a greenhouse method of testing. Using the procedures described below, the enols of the present invention were evaluated for control of the following weeds:

| | Monocots |
|---|---|
| Barnyardgrass | (*Echinochloa crus-galli*) |
| Foxtail | (*Setaria viridis*) |
| Johnsongrass or | (*Sorghum halepense*) |
| Sudangrass | (*Sorghum sudanese*) |
| Nutsedge | (*Cyperus esculentus*) |
| Wild Oat | (*Avena fatua*) |
| | Dicots |
| Cocklebur | (*Xanthium pennsylvanicum*) |
| Morningglory | (*Ipomoea spp.*) |
| Sicklepod | (*Cassia obtusifolia*) |
| Velvetleaf | (*Abutilon theophrasti*) |
| Pigweed | (*Amaranthus retroflexus*) |

The following test procedure was employed. Seeds of selected weeds and soybean are planted in flats and covered with 0.5 inches of a 3:1 soil-sand mixture. For preemergence tests, immediately after planting, the test compound is sprayed directly onto the soil surface. The flats are then watered by subirrigation and overhead. Subsequently, only overhead watering is used. For preplant incorporated tests, a double layer of cheesecloth is placed between the seeds and covering soil-sand mixture so that immediately following the spray application to the soil surface, the soil is lifted from the flat via the cheesecloth, transferred to a 1 gallon plastic bag and tumbled therein for approximately 15 seconds. The tumbled soil is then returned to the flat as a covering over the seeds. Subsequent growth conditions are the same as that described for preemergence tests. For postemergence tests, the seeds are allowed to germinate and grow for 14 to 21 days. Each series of test plants were selected for uniformity, size and stage of development. The flats are then treated with the test compound. The flats for postemergence tests are watered by subirrigation only.

The compound to be evaluated was dissolved in about 5.0 ml of 50:50 acetone-methanol solution with 0.05% (weight by volume) of an alkylaryl polyether alcohol surfactant (Triton ® X-114, commercially available from Rohm and Haas Company). This solution is then diluted with about 200 ml of acetone and sprayed over the flats using a carrier volume equivalent to 50 gallons per acre at the rate of application in pounds per acre (lb./A) specified in the table. About two weeks after application of the test compound, the state of growth of the plant is observed. Each species is evaluated on a scale of 0–100 in which 0 equals no activity and 100 equals total kill. The results for the monocots and dicots were averaged separately and reported as AM and AD respectively. The following table (Table II) shows the results obtained for the test compounds at the stated rate of application.

TABLE II

| Compound of Example No. | Rate (lb./A) | Herbicidal Activity | | |
|---|---|---|---|---|
| | | | Preemergence | Postemergence |
| 1 | 8 | AM | 19 | |
| | | AD | 23 | |
| | 4 | AM | | 20 |
| | | AD | | 58 |
| 2 | 8 | AM | 13 | |
| | | AD | 12 | |
| | 4 | AM | | 17 |
| | | AD | | 47 |
| 3 | 8 | AM | 9 | |
| | | AD | 10 | |
| | 4 | AM | | 3 |
| | | AD | | 36 |
| 4 | 8 | AM | 24 | |
| | | AD | 11 | |
| | 4 | AM | | 6 |
| | | AD | | 16 |
| 5 | 8 | AM | 40 | |
| | | AD | 53 | |
| | 4 | AM | | 10 |
| | | AD | | 32 |
| 6 | 8 | AM | 2 | |
| | | AD | 10 | |
| | 4 | AM | | 5 |
| | | AD | | 10 |
| 7 | 8 | AM | 0 | |
| | | AD | 0 | |
| | 4 | AM | | 2 |
| | | AD | | 8 |
| 8 | 8 | AM | 16 | |
| | | AD | 4 | |
| | 4 | AM | | 21 |
| | | AD | | 40 |
| 9 | 8 | AM | 19 | |
| | | AD | 6 | |
| | 4 | AM | | 3 |
| | | AD | | 28 |
| 10 | 8 | AM | 11 | |
| | | AD | 0 | |
| | 4 | AM | | 3 |
| | | AD | | 0 |
| 11 | 4 | AM | 5 | 22 |
| | | AD | 0 | 28 |
| 12 | 4 | AM | 82 | 66 |
| | | AD | 50 | 78 |
| 13 | 4 | AM | 62 | 51 |
| | | AD | 26 | 66 |
| 14 | 4 | AM | 0 | 9 |
| | | AD | 4 | 8 |
| 15 | 8 | AM | 31 | |
| | | AD | 15 | |
| | 4 | AM | | 0 |
| | | AD | | 2 |
| 16 | 8 | AM | 17 | |
| | | AD | 17 | |
| | 4 | AM | | 2 |
| | | AD | | 0 |
| 17 | 8 | AM | 57 | |
| | | AD | 53 | |
| | 4 | AM | | 3 |
| | | AD | | 31 |
| 18 | 8 | AM | 25 | |
| | | AD | 21 | |
| | 4 | AM | | 0 |
| | | AD | | 1 |
| 19 | 8 | AM | 34 | |
| | | AD | 26 | |
| 20 | 4 | AM | | 0 |
| | | AD | | 0 |
| | 8 | AM | 13 | |
| | | AD | 0 | |
| 21 | 4 | AM | | 0 |
| | | AD | | 0 |
| | 8 | AM | 9 | |
| | | AD | 2 | |
| 22 | 4 | AM | | 1 |
| | | AD | | 0 |
| | 8 | AM | 13 | |
| | | AD | 14 | |
| 23 | 4 | AM | | 0 |
| | | AD | | 3 |
| | 8 | AM | 0 | |
| | | AD | 0 | |
| 24 | 4 | AM | | 0 |
| | | AD | | 0 |
| | 8 | AM | 15 | |
| | | AD | 1 | |
| 25 | 4 | AM | | 0 |
| | | AD | | 11 |
| | 8 | AM | 0 | |
| | | AD | 0 | |
| 26 | 4 | AM | | 0 |
| | | AD | | 2 |
| | 8 | AM | 5 | |
| | | AD | 0 | |
| 27 | 4 | AM | | 4 |
| | | AD | | 2 |
| | 8 | AM | 16 | |
| | | AD | 0 | |
| 28 | 4 | AM | | 0 |
| | | AD | | 17 |
| | 8 | AM | 15 | |
| | | AD | 3 | |
| 29 | 4 | AM | | 0 |
| | | AD | | 0 |
| | 8 | AM | 31 | |
| | | AD | 15 | |
| 30 | 4 | AM | | 0 |
| | | AD | | 2 |
| | 8 | AM | 16 | |
| | | AD | 0 | |
| 31 | 4 | AM | | 2 |
| | | AD | | 2 |
| | 8 | AM | 11 | |
| | | AD | 0 | |
| 32 | 4 | AM | | 2 |
| | | AD | | 0 |
| | 8 | AM | 27 | |
| | | AD | 28 | |
| 33 | 4 | AM | | 13 |
| | | AD | | 23 |
| | 8 | AM | 16 | |
| | | AD | 61 | |
| 34 | 4 | AM | | 0 |
| | | AD | | 29 |
| | 8 | AM | 43 | |
| | | AD | 70 | |
| 35 | 4 | AM | | 1 |
| | | AD | | 10 |
| | 8 | AM | 39 | |
| | | AD | 88 | |
| 36 | 4 | AM | | 1 |
| | | AD | | 84 |
| | 8 | AM | 15 | |
| | | AD | 0 | |
| 37 | 4 | AM | | 3 |
| | | AD | | 1 |
| | 8 | AM | 34 | |
| | | AD | 68 | |
| 38 | 4 | AM | | 0 |
| | | AD | | 32 |
| | 8 | AM | 40 | |
| | | AD | 45 | |
| | 4 | AM | | 5 |
| | | AD | | 19 |

TABLE II-continued

Herbicidal Activity

| Compound of Example No. | Rate (lb./A) | | Preemergence | Postemergence |
|---|---|---|---|---|
| 39 | 8 | AM | 80 | |
| | | AD | 72 | |
| | 4 | AM | | 18 |
| | | AD | | 21 |
| 40 | 8 | AM | 16 | |
| | | AD | 47 | |
| | 4 | AM | | 0 |
| | | AD | | 3 |
| 41 | 8 | AM | 16 | |
| | | AD | 34 | |
| | 4 | AM | | 10 |
| | | AD | | 14 |
| 42 | 8 | AM | 0 | |
| | | AD | 0 | |
| | 4 | AM | | 0 |
| | | AD | | 0 |
| 43 | 4 | AM | 3 | —[a] |
| | | AD | 0 | — |
| 44 | 4 | AM | 36 | 30 |
| | | AD | 59 | 47 |
| 45 | 4 | AM | 13 | 2 |
| | | AD | 7 | 3 |
| 46 | 8 | AM | 14 | |
| | | AD | 0 | |
| | 4 | AM | | 0 |
| | | AD | | 0 |
| 47 | 8 | AM | 42 | |
| | | AD | 77 | |
| | 4 | AM | | 5 |
| | | AD | | 8 |
| 48 | 8 | AM | 26 | |
| | | AD | 38 | |
| | 4 | AM | | 2 |
| | | AD | | 25 |
| 49 | 8 | AM | 23 | |
| | | AD | 73 | |
| | 4 | AM | | 2 |
| | | AD | | 11 |
| 50 | 8 | AM | 41 | |
| | | AD | 71 | |
| | 4 | AM | | 9 |
| | | AD | | 35 |
| 51 | 8 | AM | 16 | |
| | | AD | 33 | |
| | 4 | AM | | 0 |
| | | AD | | 2 |
| 52 | 8 | AM | 0 | |
| | | AD | 0 | |
| | 4 | AM | | 0 |
| | | AD | | 0 |
| 53 | 8 | AM | 9 | |
| | | AD | 39 | |
| | 4 | AM | | 0 |
| | | AD | | 0 |
| 54 | 8 | AM | 68 | |
| | | AD | 57 | |
| | 4 | AM | | 7 |
| | | AD | | 8 |
| 55 | 4 | AM | 99 | 95 |
| | | AD | 77 | 84 |
| | 1 | AM | 96 | 78 |
| | | AD | 60 | 74 |
| 56 | 4 | AM | 97 | 52 |
| | | AD | 55 | 71 |
| 57 | 4 | AM | 19 | 0 |
| | | AD | 0 | 8 |
| 58 | 2 | AM | 40 | 9 |
| | | AD | 12 | 55 |
| 59 | 4 | AM | 35 | 4 |
| | | AD | 16 | 12 |
| 60 | 4 | AM | 19 | 0 |
| | | AD | 0 | 8 |
| 61 | 4 | AM | 19 | 0 |
| | | AD | 3 | 6 |
| 62 | 4 | AM | 0 | 4 |
| | | AD | 0 | 3 |
| 63 | 4 | AM | 30 | 2 |
| | | AD | 12 | 35 |
| 64 | 4 | AM | 31 | 3 |
| | | AD | 30 | 38 |
| 65 | 4 | AM | 12 | 1 |
| | | AD | 24 | 29 |
| 66 | 4 | AM | 0 | 0 |
| | | AD | 0 | 14 |
| 67 | 4 | AM | 30 | 9 |
| | | AD | 35 | 68 |
| 68 | 4 | AM | 49 | 61 |
| | | AD | 46 | 42 |
| 69 | 4 | AM | 91 | 66 |
| | | AD | 59 | 66 |
| 70 | 4 | AM | 14 | 12 |
| | | AD | 9 | 10 |
| 71 | 4 | AM | 25 | 19 |
| | | AD | 21 | 44 |
| 72 | 4 | AM | 5 | 1 |
| | | AD | 4 | 7 |
| 73 | 4 | AM | 0 | 0 |
| | | AD | 9 | 10 |
| 74 | 4 | AM | 0 | 0 |
| | | AD | 0 | 0 |
| 75 | 4 | AM | 19 | 2 |
| | | AD | 23 | 15 |
| 76 | 4 | AM | 76 | 21 |
| | | AD | 25 | 25 |
| 77 | 4 | AM | 94 | 50 |
| | | AD | 29 | 49 |
| 78 | 4 | AM | 58 | 5 |
| | | AD | 25 | 9 |
| 79 | 4 | AM | 5 | 0 |
| | | AD | 25 | 67 |
| 80 | 4 | AM | 0 | 3 |
| | | AD | 0 | 4 |
| 81 | 4 | AM | 0 | 0 |
| | | AD | 15 | 0 |
| 82 | 4 | AM | 1 | 0 |
| | | AD | 0 | 5 |
| 83 | 4 | AM | 23 | 17 |
| | | AD | 9 | 37 |
| 84 | 4 | AM | 3 | 0 |
| | | AD | 0 | 3 |
| 85 | 4 | AM | 0 | 0 |
| | | AD | 0 | 24 |
| 86 | 4 | AM | 0 | 0 |
| | | AD | 0 | 0 |
| 87 | 4 | AM | 12 | 3 |
| | | AD | 25 | 19 |
| | 1 | AM | 17 | 0 |
| | | AD | 20 | 5 |
| 88 | 4 | AM | 91 | — |
| | | AD | 87 | — |
| | 1 | AM | 55 | |
| | | AD | 85 | |
| 89 | 4 | AM | 92 | 80 |
| | | AD | 81 | 97 |
| | 1 | AM | 40 | 38 |
| | | AD | 43 | 57 |
| 90 | 4 | AM | 56 | 19 |
| | | AD | 42 | 43 |
| 91 | 4 | AM | 9 | 6 |
| | | AD | 5 | 49 |
| 92 | 4 | AM | 0 | 3 |
| | | AD | 0 | 20 |
| 93 | 2 | AM | 3 | 8 |
| | | AD | 5 | 18 |
| 94 | 2 | AM | 78 | 73 |
| | | AD | 29 | 56 |
| | 0.5 | AM | 72 | 45 |
| | | AD | 8 | 45 |
| 95 | 2 | AM | 80 | 36 |
| | | AD | 47 | 34 |
| | 0.5 | AM | 58 | 15 |
| | | AD | 22 | 11 |
| 96 | 2 | AM | 60 | 0 |
| | | AD | 25 | 3 |
| | 0.5 | AM | 42 | 3 |
| | | AD | 21 | 3 |

TABLE II-continued

Herbicidal Activity

| Compound of Example No. | Rate (lb./A) | | Preemergence | Postemergence |
|---|---|---|---|---|
| 97 | 2 | AM | 77 | 36 |
|  |  | AD | 55 | 17 |
| 98 | 4 | AM | 91 | — |
|  |  | AD | 87 | — |
| 99 | 2 | AM | 86 | 55 |
|  |  | AD | 59 | 38 |
| 100 | 2 | AM | 70 | — |
|  |  | AD | 37 | — |
| 101 | 2 | AM | 96 | 74 |
|  |  | AD | 25 | 45 |
| 102 | .5 | AM | 0 | 0 |
|  |  | AD | 0 | 3 |
|  | 2 | AM | 0 | 0 |
|  |  | AD | 0 | 10 |
| 103 | .5 | AM | 36 | 8 |
|  |  | AD | 21 | 11 |
|  | 2 | AM | 73 | 29 |
|  |  | AD | 21 | 49 |
| 104 | .5 | AM | 57 | 2 |
|  |  | AD | 1 | 2 |
|  | 2 | AM | 92 | 5 |
|  |  | AD | 9 | 5 |
| 105 | .5 | AM | 72 | 35 |
|  |  | AD | 65 | 35 |
|  | 2 | AM | 83 | 59 |
|  |  | AD | 69 | 43 |
| 106 | .5 | AM | 1 | 1 |
|  |  | AD | 21 | 13 |
|  | 2 | AM | 27 | 15 |
|  |  | AD | 29 | 25 |
| 107 | .5 | AM | 19 | 15 |
|  |  | AD | 10 | 8 |
|  | 2 | AM | 39 | 28 |
|  |  | AD | 23 | 27 |
| 108 | .5 | AM | 62 | 10 |
|  |  | AD | 66 | 50 |
|  | 2 | AM | 71 | 56 |
|  |  | AD | 64 | 65 |
| 109 | 2 | AM | 96 | 67 |
|  |  | AD | 70 | 37 |
| 110 | 2 | AM | 92 | 59 |
|  |  | AD | 63 | 58 |
| 111 | 2 | AM | 78 | 24 |
|  |  | AD | 87 | 44 |
| 112 | 4 | AM | 64 | 9 |
|  |  | AD | 66 | 35 |
| 113 | 4 | AM | 5 | 9 |
|  |  | AD | 75 | 75 |
| 114 | 2 | AM | 78 | 63 |
|  |  | AD | 59 | 66 |

[a]No data recorded.

It is to be understood that changes and variations may be made without departing from the spirit and scope of the invention as defined by the appended claims.

I claim:

1. A compound having the formula:

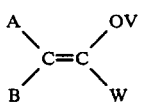

wherein
A is $COR^1$, $CO_2R^1$ or $CONR^4R^5$;
B is cyano; COR; $CO_2R$; or $S(O)_nR^2$;
V is hydrogen, $(C_1-C_6)$alkyl, $COR^3$ or phenalkyl having one to four carbons in the alkyl group;
W is unsubstituted or substituted furan, unsubstituted or substituted thiophene wherein the substituent is halo or nitro; or substituted phenyl having the formula

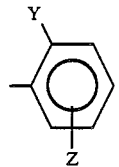

wherein
Y is halo, nitro, $(C_1-C_4)$alkoxy or $(C_1-C_4)$haloalkyl;
Z is from one to two of the same or different hydrogen, halo, cyano, $(C_1-C_6)$haloalkyl, nitro, $(C_1-C_6)$alkyl, $(C_1-C_6)$alkoxy or $(C_1-C_6)$haloalkoxy;
R is $(C_1-C_4)$alkyl;
$R^1$ is $(C_1-C_4)$alkyl;
$R^3$ is $(C_1-C_6)$alkyl or unsubstituted or substituted phenyl having one to three of the same or different halo, nitro, $(C_1-C_4)$alkyl, $(C_1-C_4)$alkoxy, $(C_1-C_4)$haloalkyl, or dialkylamino having independently up to six carbons in each alkyl moiety;
$R^4$ and $R^5$ are independently, $(C_1-C_3)$alkyl or $R^4$ and $R^5$ joined together with the nitrogen to which they are attached form a heteroalkyl ring selected from the group consisting of morpholine, piperidine and pyrrolidine;
n is from 0 to 2; geometric isomers, tautomers, halogen addition products and agronomically acceptable salts thereof.

2. A compound according to claim 1 wherein:
A is $COR^1$ or $CONR^4R^5$;
B is cyano;
V is hydrogen;
W is

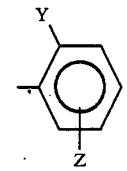

where
Y is nitro or $(C_1-C_4)$haloalkyl; and
Z is from one to two of the same or different halo, $(C_1-C_6)$haloalkyl, or $(C_1-C_6)$haloalkoxy;
$R^1$ is $(C_1-C_4)$branched alkyl;
R4 and R5 are independently $(C_1-C_3)$, and agronomically acceptable salts thereof.

3. A compound according to claim 2 wherein:
A is dimethylcarbamoyl;
B is cyano;
V is hydrogen; and
W is 2-nitro-4-chlorophenyl.

4. A compound according to claim 2 wherein:
A is dimethylcarbamoyl;
B is cyano;
V is hydrogen; and
W is 2-nitro-4-trifluoromethylphenyl.

5. A compound having the formula:

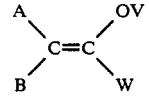

wherein

A is $COR^1$, or $CONR^4R^5$;
B is cyano, COR; $CO_2R$; or $S(O)_nR^2$
V is hydrogen, $(C_1-C_6)$alkyl, $COR^3$ or phenalkyl having one to four carbons in the alkyl group;
W is unsubstituted or substituted furan, unsubstituted or substituted thiophene wherein the substituent is halo or nitro; or substituted phenyl having the formula

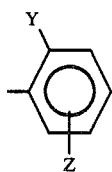

wherein
Y is halo, nitro, $(C_1-C_4)$alkoxy or $(C_1-C_4)$haloalkyl;
Z is from one to two of the same or different hydrogen, halo, cyano, $(C_1-C_6)$haloalkyl $(C_1-C_6)$alkoxy or $(C_1-C_6)$haloalkoxy;
R is $(C_1-C_4)$alkyl;
$R^1$ is $(C_1-C_4)$alkyl;
$R^3$ is $(C_1-C_6)$alkyl or unsubstituted or substituted phenyl having one to three of the same or different halo, nitro, $(C_1-C_4)$alkyl, $(C_1-C_4)$alkoxy, $(C_1-C_4)$haloalkyl, or dialkylamino having independently up to six carbons in each alkyl moiety;
$R^4$ and $R^5$ are independently, $(C_1-C_3)$alkyl or $R^4$ and $R^5$ joined together with the nitrogen to which they are attached form a heteroalkyl ring selected from the group consisting of morpholine, piperidine and pyrrolidine;
n is from 0 to 2; geometric isomers, tautomers, halogen addition products and agronomically acceptable salts thereof.

6. A compound of the formula

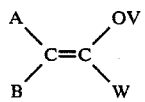

wherein:
A is $COR^1$;
B is cyano;
V is hydrogen;
W is

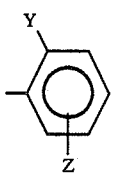

wherein
Y is nitro or $(C_1-C_4)$haloalkyl;
Z is from one to two of the same or different halo, $(C_1-C_6)$haloalkyl, or $(C_1-C_6)$haloalkoxy;
$R^1$ is $(C_1-C_4)$ branched alkyl; and agronomically acceptable salts thereof.

7. A compound according to claim 6 wherein:
A is t-butylcarbonyl;
B is cyano;
V is hydrogen; and
W is 2-nitro-4-chlorophenyl.

8. A compound according to claim 6 wherein:
A is t-butylcarbonyl;
B is cyano;
V is magnesium; and
W is 2-nitro-4-chlorophenyl.

9. A compound according to claim 6 wherein:
A is t-butylcarbonyl;
B is cyano;
V lithium; and
W is 2-nitro-4-chlorophenyl.

10. A compound according to claim 6 wherein:
A is t-butylcarbonyl;
B is cyano;
V is $(CH_3)_3N^{\oplus}CH_2PMR$; and
W is 2-nitro-4-chlorophenyl.

11. A compound according to claim 6 wherein:
A is t-butylcarbonyl;
B is cyano;
V is copper (II); and
W is 2-nitro-4-chlorophenyl.

12. A compound according to claim 6 wherein:
A is t-butylcarbonyl;
B is cyano;
V is $(CH_3)_2NH^{\oplus}CH_2PMR$; and
W is 2-nitro-4-chlorophenyl.

13. A compound according to claim 6 wherein:
A is t-butylcarbonyl;
B is cyano;
V is hydrogen; and
W is 2-nitro-4-trifluoromethylphenyl.

14. A compound according to claim 6 wherein:
A is t-butylcarbonyl;
B is cyano;
V is hydrogen; and
W is 2-nitro-4-fluorophenyl.

15. A compound according to claim 2 wherein:
A is t-butylcarbonyl;
B is cyano;
V is hydrogen; and
W is 2-nitro-4-difluoromethoxyphenyl.

16. A compound according to claim 2 wherein:
A is t-butylcarbonyl;
B is cyano;
V is hydrogen; and
W is 2-nitro-4-tetrafluoroethoxyphenyl.

17. A method of controlling weeds which comprises applying to the locus to be controlled a herbicidally effective amount of a compound according to claim 1.

18. The method of claim 17 wherein the compound is applied at a rate of from about 0.01 to about 12 pounds per acre.

19. The method of claim 18 wherein the compound is applied at a rate of from about 0.01 to about 5 pounds per acre.

20. The method of claim 17 wherein said compound is applied preemergence.

21. The method of claim 17 wherein said weed is *Cyperus spp.*

22. A herbicidal composition comprising a compound according to claim 1 and an agronomically acceptable carrier.

23. The composition according to claim 22 which also comprises a surfactant.

24. The composition according to claim 22 wherein said compound is present at from about 1% to about 98% by weight of the composition.

25. A method of controlling weeds which comprises applying to the locus to be controlled a herbicidally effective amount of a composition according to claim 22.

26. A compound of the formula

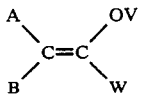

wherein:
A is $COR^1$, $CO_2R^1$ or $CONR^4R^5$;
B is cyano, COR, $CO_2R$ or $S(O)_nR^2$;
V is hydrogen; $(C_1-C_6)$alkyl; alkylcarbonylalkyl having, independently, one to four carbon atoms in each alkyl group; alkoxycarbonylalkyl having, independently, one to four carbon atoms in each alkyl group; $COR^3$; or phenalkyl having one to four carbon atoms in the alkyl group;
W is unsubstituted or substituted furan, unsubstituted or substituted thiophene wherein the substituent is halo or nitro; or a substituted phenyl having the formula

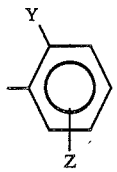

wherein
Y is halo, nitro, $(C_1-C_4)$haloalkyl, $(C_1-C_4)$alkoxy;
Z is one to two of the same or different hydrogen, halo, nitro, cyano, $(C_1-C_6)$alkyl, $(C_1-C_6)$alkoxy, $(C_1-C_6)$haloalkyl, $(C_1-C_6)$haloalkoxy;
R is hydrogen or $(C_1-C_4)$alkyl;
$R^1$ is $(C_1-C_4)$alkyl or unsubstituted or substituted $(C_3-C_4)$cycloalkyl wherein the substituent is halo, cyano or $(C_1-C_2)$alkyl;
$R^2$ is independently $(C_1-C_2)$alkyl, $(C_1-C_4)$haloalkyl; $(C_1-C_4)$cycanoalkyl; unsubstituted or substituted $(C_3-C_8)$cycloalkyl where the substituent is halo, cyano or $(C_1-C_4)$alkyl; or unsubstituted or substituted phenyl having one to three of the same or different halo, nitro, cyano, trifluoromethyl, $(C_1-C_4)$alkyl, $(C_1-C_4)$alkoxy or $S(O)_nR^2$;
$R_3$ is $(C_1-C_6)$alkyl; $(C_1-C_6)$haloalkyl; $(C_1-C_6)$alkoxy; amino; $(C_1-C_6)$alkylamino, dialkylamino having, independently, up to six carbon atoms in each alkyl moiety; or unsubstituted or substituted aryl having one to five of the same or different halo, nitro, cyano, $S(O)_nR^2$, $(C_1-C_6)$alkyl, $(C_1-C_6)$alkoxy, $(C_1-C_6)$haloalkyl, carboxy, $(C_1-C_6)$alkanoyloxy or $(C_1-C_6)$alkoxycarbonyl;
$R^4$ and $R^5$ are independently $(C_1-C_3)$alkyl or $R^4$ and $R^5$ can be joined together with the nitrogen to which they are attached to form a heteroalkyl ring selected from the group consisting of morpholine, piperidine and pyrrolidine;
n is from 0 to 2;
geometric isomer, tautomers, halogen addition products and agronomically acceptable salts thereof.

* * * * *